US010485959B2

(12) United States Patent
Wang

(10) Patent No.: US 10,485,959 B2
(45) Date of Patent: *Nov. 26, 2019

(54) DRUG RELEASING COATINGS FOR BALLOON CATHETERS

(71) Applicant: Lutonix, Inc., New Hope, MN (US)

(72) Inventor: Lixiao Wang, Medina, MN (US)

(73) Assignee: LUTONIX, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/654,233

(22) Filed: Jul. 19, 2017

(65) Prior Publication Data

US 2018/0036516 A1 Feb. 8, 2018

Related U.S. Application Data

(63) Continuation of application No. 15/154,669, filed on May 13, 2016, now Pat. No. 9,737,691, and a continuation-in-part of application No. 15/067,739, filed on Mar. 11, 2016, now Pat. No. 9,757,544, which is a continuation of application No. 14/683,612, filed on Apr. 10, 2015, now Pat. No. 9,289,539, which is a continuation of application No. 13/846,143, filed on Mar. 18, 2013, now Pat. No. 9,005,161, which is a continuation of application No. 12/731,835, filed on Mar. 25, 2010, now Pat. No. 8,414,910, which is a continuation-in-part of application No. 12/121,986, filed on May 16, 2008, now Pat. No. 8,414,525, which is a continuation-in-part of application No. 11/942,452, filed on Nov. 19, 2007, now Pat. No. 8,414,909, which is a continuation-in-part of application No. 14/932,033, filed on Nov. 4, 2015, now Pat. No. 9,770,576, which is a continuation of application No. 13/846,358, filed on Mar. 18, 2013, now Pat. No. 9,180,485, which is a continuation of application No. 12/549,180, filed on Aug. 27, 2009, now Pat. No. 8,430,055.

(Continued)

(51) Int. Cl.

| A61M 25/10 | (2013.01) |
|---|---|
| A61F 2/958 | (2013.01) |
| A61K 31/337 | (2006.01) |
| A61F 2/844 | (2013.01) |
| A61L 29/08 | (2006.01) |
| A61L 29/16 | (2006.01) |
| A61L 31/16 | (2006.01) |
| A61L 31/10 | (2006.01) |
| A61L 31/08 | (2006.01) |
| A61K 31/436 | (2006.01) |

(52) U.S. Cl.
CPC ............ *A61M 25/10* (2013.01); *A61F 2/844* (2013.01); *A61F 2/958* (2013.01); *A61K 31/337* (2013.01); *A61K 31/436* (2013.01); *A61L 29/08* (2013.01); *A61L 29/085* (2013.01); *A61L 29/16* (2013.01); *A61L 31/08* (2013.01); *A61L 31/10* (2013.01); *A61L 31/16* (2013.01); *A61K 2300/00* (2013.01); *A61L 2300/416* (2013.01); *A61L 2300/428* (2013.01); *A61L 2300/606* (2013.01); *A61L 2300/608* (2013.01); *A61L 2300/802* (2013.01); *A61M 2025/105* (2013.01)

(58) Field of Classification Search
CPC ....... A61F 2/844; A61F 2/958; A61K 31/337; A61K 31/436; A61K 2300/00; A61L 29/08; A61L 29/085; A61L 29/16; A61L 31/08; A61L 31/10; A61L 31/16; A61L 2300/416; A61L 2300/428; A61L 2300/606; A61L 2300/608; A61L 2300/802; A61M 25/10; A61M 2025/105
See application file for complete search history.

(56) References Cited

U.S. PATENT DOCUMENTS

| 3,929,992 A | 12/1975 | Sehgal et al. |
| 3,993,749 A | 11/1976 | Sehgal et al. |

(Continued)

FOREIGN PATENT DOCUMENTS

| AU | 2009201214 A1 | 10/2009 |
| CN | 101185779 A | 5/2008 |

(Continued)

OTHER PUBLICATIONS

Cardoso et al., Clinical application of airway bypass with paclitaxel-eluting stents: Early results, The Journal of Thoracic and Cardiovascular Surgery, Sep. 2007, pp. 974-981, vol. 134 No. 4, The American Association for Thoracic Surgery, St. Louis.

(Continued)

*Primary Examiner* — Matthew P Coughlin
*Assistant Examiner* — Thurman Wheeler
(74) *Attorney, Agent, or Firm* — Dinsmore & Shohl LLP

(57) ABSTRACT

Balloon catheters, methods for preparing balloon catheters, and uses of balloon catheters are disclosed. The balloon catheter includes an elongate member, an expandable balloon, and a coating layer overlying an exterior surface of the expandable balloon. The coating layer includes a total drug load of a hydrophobic therapeutic agent and a combination of additives including a first additive and a second additive. The hydrophobic therapeutic agent is paclitaxel, rapamycin, or paclitaxel and rapamycin. The first additive is a surfactant. The second additive is a chemical compound having one or more hydroxyl, amino, carbonyl, carboxyl, acid, amide, or ester groups.

20 Claims, 2 Drawing Sheets

Related U.S. Application Data

(60) Provisional application No. 61/092,872, filed on Aug. 29, 2008, provisional application No. 60/981,380, filed on Oct. 19, 2007, provisional application No. 60/981,384, filed on Oct. 19, 2007, provisional application No. 60/926,850, filed on Apr. 30, 2007, provisional application No. 60/904,473, filed on Mar. 2, 2007, provisional application No. 60/903,529, filed on Feb. 26, 2007, provisional application No. 60/897,427, filed on Jan. 25, 2007, provisional application No. 60/880,742, filed on Jan. 17, 2007, provisional application No. 60/860,084, filed on Nov. 20, 2006.

(56) References Cited

U.S. PATENT DOCUMENTS

| | | |
|---|---|---|
| 4,252,969 A | 2/1981 | Broering et al. |
| 4,300,820 A | 11/1981 | Shah |
| 4,308,184 A | 12/1981 | Thoma et al. |
| 4,316,885 A | 2/1982 | Rakhit |
| 4,364,921 A | 12/1982 | Speck et al. |
| 4,921,483 A | 5/1990 | Wijay et al. |
| 5,023,262 A | 6/1991 | Caufield et al. |
| 5,023,263 A | 6/1991 | Von Burg |
| 5,023,264 A | 6/1991 | Caufield et al. |
| 5,026,607 A | 6/1991 | Kiezulas |
| 5,061,738 A | 10/1991 | Solomon et al. |
| 5,080,899 A | 1/1992 | Sturm et al. |
| 5,092,841 A | 3/1992 | Spears |
| 5,100,883 A | 3/1992 | Schiehser |
| 5,102,402 A | 4/1992 | Dror et al. |
| 5,102,876 A | 4/1992 | Caufield |
| 5,118,677 A | 6/1992 | Caufield |
| 5,118,678 A | 6/1992 | Kao et al. |
| 5,120,322 A | 6/1992 | Davis et al. |
| 5,120,725 A | 6/1992 | Kao et al. |
| 5,120,726 A | 6/1992 | Failli et al. |
| 5,120,727 A | 6/1992 | Kao et al. |
| 5,120,842 A | 6/1992 | Failli et al. |
| 5,130,307 A | 7/1992 | Failli et al. |
| 5,135,516 A | 8/1992 | Sahatjian et al. |
| 5,138,051 A | 8/1992 | Hughes et al. |
| 5,151,413 A | 9/1992 | Caufield et al. |
| 5,162,333 A | 11/1992 | Failli et al. |
| 5,164,299 A | 11/1992 | Lambert |
| 5,164,399 A | 11/1992 | Failli et al. |
| 5,177,203 A | 1/1993 | Failli et al. |
| 5,193,447 A | 3/1993 | Lucas et al. |
| 5,194,447 A | 3/1993 | Kao |
| 5,196,596 A | 3/1993 | Abatjoglou |
| 5,199,951 A | 4/1993 | Spears |
| 5,221,670 A | 6/1993 | Caufield |
| 5,221,740 A | 6/1993 | Hughes |
| 5,233,036 A | 8/1993 | Hughes |
| 5,252,579 A | 10/1993 | Skotnicki et al. |
| 5,254,089 A | 10/1993 | Wang |
| 5,260,300 A | 11/1993 | Hu |
| 5,262,423 A | 11/1993 | Kao |
| 5,269,770 A | 12/1993 | Conway et al. |
| 5,302,584 A | 4/1994 | Kao et al. |
| 5,304,121 A | 4/1994 | Sahatjian |
| 5,324,261 A | 6/1994 | Amundson et al. |
| 5,346,893 A | 9/1994 | Failli et al. |
| 5,349,060 A | 9/1994 | Kao et al. |
| 5,362,718 A | 11/1994 | Skotnicki et al. |
| 5,370,614 A | 12/1994 | Amundson et al. |
| 5,373,014 A | 12/1994 | Failli et al. |
| 5,378,696 A | 1/1995 | Caufield |
| 5,378,836 A | 1/1995 | Kao et al. |
| 5,380,298 A | 1/1995 | Zabetakis et al. |
| 5,380,299 A | 1/1995 | Fearnot et al. |
| 5,385,908 A | 1/1995 | Nelson et al. |
| 5,385,909 A | 1/1995 | Nelson et al. |
| 5,385,910 A | 1/1995 | Ocain et al. |
| 5,387,680 A | 2/1995 | Nelson |
| 5,389,639 A | 2/1995 | Failli et al. |
| 5,391,730 A | 2/1995 | Skotnicki et al. |
| 5,411,967 A | 5/1995 | Kao et al. |
| 5,441,759 A | 8/1995 | Crouther et al. |
| 5,446,048 A | 8/1995 | Failli et al. |
| 5,463,048 A | 10/1995 | Skotnicki et al. |
| 5,464,650 A | 11/1995 | Berg et al. |
| 5,480,988 A | 1/1996 | Failli et al. |
| 5,480,989 A | 1/1996 | Kao et al. |
| 5,482,945 A | 1/1996 | Armstrong et al. |
| 5,489,680 A | 2/1996 | Failli et al. |
| 5,490,839 A | 2/1996 | Wang et al. |
| 5,491,231 A | 2/1996 | Nelson et al. |
| 5,496,276 A | 3/1996 | Wang et al. |
| 5,504,091 A | 4/1996 | Molnar-Kimber et al. |
| 5,504,092 A | 4/1996 | Nilsson et al. |
| 5,504,204 A | 4/1996 | Failli et al. |
| 5,508,399 A | 4/1996 | Kao et al. |
| 5,509,899 A | 4/1996 | Fan et al. |
| 5,516,781 A | 5/1996 | Morris et al. |
| 5,525,348 A | 6/1996 | Whitbourne et al. |
| 5,525,610 A | 6/1996 | Caufield et al. |
| 5,530,007 A | 6/1996 | Kao et al. |
| 5,530,121 A | 6/1996 | Kao et al. |
| 5,532,355 A | 7/1996 | Skotnicki et al. |
| 5,536,729 A | 7/1996 | Waranis et al. |
| 5,559,121 A | 9/1996 | Harrison et al. |
| 5,559,227 A | 9/1996 | Failli et al. |
| 5,563,145 A | 10/1996 | Failli et al. |
| 5,563,146 A | 10/1996 | Morris et al. |
| 5,567,709 A | 10/1996 | Skotnicki et al. |
| 5,573,518 A | 11/1996 | Haaga |
| 5,599,307 A | 2/1997 | Bacher et al. |
| 5,607,463 A | 3/1997 | Schwartz et al. |
| 5,609,629 A | 3/1997 | Fearnot et al. |
| 5,616,608 A | 4/1997 | Kinsella et al. |
| 5,632,772 A | 5/1997 | Alcime et al. |
| 5,674,192 A | 10/1997 | Sahatjian et al. |
| 5,674,287 A | 10/1997 | Slepian et al. |
| 5,679,400 A | 10/1997 | Tuch |
| 5,681,846 A | 10/1997 | Trissel |
| 5,693,034 A | 12/1997 | Buscemi et al. |
| 5,698,582 A | 12/1997 | Bastart et al. |
| 5,702,754 A | 12/1997 | Zhong |
| 5,716,981 A | 2/1998 | Hunter et al. |
| 5,733,925 A | 3/1998 | Kunz et al. |
| 5,738,901 A | 4/1998 | Wang et al. |
| 5,752,930 A | 5/1998 | Rise et al. |
| 5,766,158 A | 6/1998 | Opolski |
| 5,776,184 A | 7/1998 | Tuch |
| 5,776,943 A | 7/1998 | Christians et al. |
| 5,780,462 A | 7/1998 | Lee et al. |
| 5,797,887 A | 8/1998 | Rosen et al. |
| 5,807,306 A | 9/1998 | Shapland et al. |
| 5,811,447 A | 9/1998 | Kunz et al. |
| 5,824,049 A | 10/1998 | Ragheb et al. |
| 5,827,289 A | 10/1998 | Reiley et al. |
| 5,843,089 A | 12/1998 | Sahatjian et al. |
| 5,865,814 A | 2/1999 | Tuch |
| 5,868,719 A | 2/1999 | Tsukernik |
| 5,869,127 A | 2/1999 | Zhong |
| 5,873,904 A | 2/1999 | Ragheb et al. |
| 5,879,697 A | 3/1999 | Ding et al. |
| 5,888,533 A | 3/1999 | Dunn |
| 5,893,840 A | 4/1999 | Hull et al. |
| 5,919,145 A | 7/1999 | Sahatjian |
| 5,919,570 A | 7/1999 | Hostettler et al. |
| 5,922,730 A | 7/1999 | Hu et al. |
| 5,947,977 A | 9/1999 | Slepian et al. |
| 5,954,706 A | 9/1999 | Sahatjian |
| 5,977,163 A | 11/1999 | Li et al. |
| 5,981,568 A | 11/1999 | Kunz et al. |
| 5,985,325 A | 11/1999 | Nagi |
| 5,989,591 A | 11/1999 | Nagi |
| 6,015,809 A | 1/2000 | Zhu et al. |
| 6,039,721 A | 3/2000 | Johnson et al. |
| 6,042,875 A | 3/2000 | Ding et al. |

(56) References Cited

U.S. PATENT DOCUMENTS

| | | |
|---|---|---|
| 6,046,230 A | 4/2000 | Chung et al. |
| 6,050,980 A | 4/2000 | Wilson |
| 6,056,722 A | 5/2000 | Jayaraman |
| 6,074,659 A | 6/2000 | Kunz et al. |
| 6,096,070 A | 8/2000 | Ragheb et al. |
| 6,120,904 A | 9/2000 | Hostettler et al. |
| 6,129,705 A | 10/2000 | Grantz |
| 6,143,037 A | 11/2000 | Goldstein et al. |
| 6,146,358 A | 11/2000 | Rowe |
| 6,176,849 B1 | 1/2001 | Yang et al. |
| 6,218,016 B1 | 4/2001 | Tedeschi et al. |
| 6,221,425 B1 | 4/2001 | Michal et al. |
| 6,221,467 B1 | 4/2001 | Nazarova et al. |
| 6,228,393 B1 | 5/2001 | DiCosmo et al. |
| 6,248,363 B1 | 6/2001 | Patel et al. |
| 6,261,630 B1 | 7/2001 | Nazarova et al. |
| 6,264,684 B1 | 7/2001 | Banas et al. |
| 6,268,390 B1 | 7/2001 | Kunz |
| 6,280,411 B1 | 8/2001 | Lennox |
| 6,287,285 B1 | 9/2001 | Michal et al. |
| 6,294,192 B1 | 9/2001 | Patel et al. |
| 6,299,604 B1 | 10/2001 | Ragheb et al. |
| 6,299,980 B1 | 10/2001 | Shah et al. |
| 6,306,144 B1 | 10/2001 | Sydney et al. |
| 6,306,166 B1 | 10/2001 | Barry et al. |
| 6,306,421 B1 | 10/2001 | Kunz et al. |
| 6,312,406 B1 | 11/2001 | Jayaraman |
| 6,328,970 B1 | 12/2001 | Molnar-Kimber et al. |
| 6,331,547 B1 | 12/2001 | Zhu et al. |
| 6,335,029 B1 | 1/2002 | Kamath et al. |
| 6,364,856 B1 | 4/2002 | Ding et al. |
| 6,364,893 B1 | 4/2002 | Sahatjian et al. |
| 6,369,039 B1 | 4/2002 | Palasis et al. |
| 6,395,326 B1 | 5/2002 | Castro et al. |
| 6,409,716 B1 | 6/2002 | Sahatjian et al. |
| 6,419,692 B1 | 7/2002 | Yang et al. |
| 6,432,973 B1 | 8/2002 | Zhu et al. |
| 6,443,941 B1 | 9/2002 | Slepian et al. |
| 6,444,324 B1 | 9/2002 | Yang et al. |
| 6,458,138 B1 | 10/2002 | Sydney et al. |
| 6,506,408 B1 | 1/2003 | Palasis |
| 6,515,009 B1 | 2/2003 | Kunz et al. |
| 6,524,274 B1 | 2/2003 | Rosenthal et al. |
| 6,528,150 B2 | 3/2003 | Nazarova et al. |
| 6,544,544 B2 | 4/2003 | Hunter et al. |
| 6,571,125 B2 | 5/2003 | Thompson |
| 6,576,224 B1 | 6/2003 | Osbakken et al. |
| 6,589,215 B2 | 7/2003 | Yang et al. |
| 6,589,546 B2 | 7/2003 | Kamath et al. |
| 6,592,548 B2 | 7/2003 | Jayaraman |
| 6,610,035 B2 | 8/2003 | Yang et al. |
| 6,616,650 B1 | 9/2003 | Rowe |
| 6,656,156 B2 | 12/2003 | Yang et al. |
| 6,663,881 B2 | 12/2003 | Kunz et al. |
| 6,677,357 B2 | 1/2004 | Zhu et al. |
| 6,680,330 B2 | 1/2004 | Zhu et al. |
| 6,682,545 B1 | 1/2004 | Kester |
| 6,699,272 B2 | 3/2004 | Slepian et al. |
| 6,730,064 B2 | 5/2004 | Ragheb et al. |
| 6,774,278 B1 | 8/2004 | Ragheb et al. |
| 6,890,339 B2 | 5/2005 | Sahatjian et al. |
| 6,890,546 B2 | 5/2005 | Mollison et al. |
| 6,893,431 B2 | 5/2005 | Naimark et al. |
| 6,899,731 B2 | 5/2005 | Li et al. |
| 6,918,869 B2 | 7/2005 | Shaw et al. |
| 6,921,390 B2 | 7/2005 | Bucay-Couto et al. |
| 6,939,320 B2 | 9/2005 | Lennox |
| 6,958,153 B1 | 10/2005 | Ormerod et al. |
| 6,991,809 B2 | 1/2006 | Anderson |
| 6,997,949 B2 | 2/2006 | Tuch |
| 7,008,411 B1 | 3/2006 | Mandrusov et al. |
| 7,025,752 B2 | 4/2006 | Rice et al. |
| 7,048,714 B2 | 5/2006 | Richter |
| 7,056,550 B2 | 6/2006 | Davila et al. |
| 7,060,051 B2 | 6/2006 | Palasis |
| 7,066,904 B2 | 6/2006 | Rosenthal et al. |
| 7,077,859 B2 | 7/2006 | Sirhan et al. |
| 7,108,684 B2 | 9/2006 | Farnan |
| 7,144,419 B2 | 12/2006 | Cheng et al. |
| 7,153,957 B2 | 12/2006 | Chew et al. |
| 7,160,317 B2 | 1/2007 | McHale et al. |
| 7,163,555 B2 | 1/2007 | Dinh |
| 7,172,619 B2 | 2/2007 | Richter |
| 7,175,873 B1 | 2/2007 | Roorda et al. |
| 7,176,261 B2 | 2/2007 | Tijsma et al. |
| 7,179,251 B2 | 2/2007 | Palasis |
| 7,198,637 B2 | 4/2007 | Deshmukh et al. |
| 7,208,009 B2 | 4/2007 | Richter |
| 7,214,198 B2 | 5/2007 | Greco et al. |
| 7,226,586 B2 | 6/2007 | Fitzhugh et al. |
| 7,232,573 B1 | 6/2007 | Ding |
| 7,235,096 B1 | 6/2007 | Van Tassel et al. |
| 7,244,444 B2 | 7/2007 | Bates |
| 7,247,313 B2 | 7/2007 | Roorda et al. |
| 7,282,213 B2 | 10/2007 | Schroeder et al. |
| 7,285,304 B1 | 10/2007 | Hossainy et al. |
| 7,292,885 B2 | 11/2007 | Scott et al. |
| 7,294,329 B1 | 11/2007 | Ding |
| 7,306,580 B2 | 12/2007 | Paul et al. |
| 7,507,433 B2 | 3/2009 | Weber |
| 7,524,527 B2 | 4/2009 | Stenzel |
| 7,547,294 B2 | 6/2009 | Seward et al. |
| 7,557,087 B2 | 7/2009 | Rothbard et al. |
| 7,803,149 B2 | 9/2010 | Bates et al. |
| 8,241,249 B2 | 8/2012 | Wang |
| 8,244,344 B2 | 8/2012 | Wang |
| 8,366,660 B2 | 2/2013 | Wang |
| 8,366,662 B2 | 2/2013 | Wang |
| 8,403,910 B2 | 3/2013 | Wang |
| 8,404,300 B2 | 3/2013 | Wang |
| 8,414,525 B2 | 4/2013 | Wang |
| 8,414,526 B2 | 4/2013 | Wang |
| 8,414,909 B2 | 4/2013 | Wang |
| 8,414,910 B2 | 4/2013 | Wang |
| 8,425,459 B2 | 4/2013 | Wang |
| 8,430,055 B2 | 4/2013 | Wang et al. |
| 8,932,561 B2 | 1/2015 | Wang |
| 8,998,846 B2 | 4/2015 | Wang |
| 9,072,812 B2 | 7/2015 | Speck et al. |
| 9,220,875 B2 | 12/2015 | Scheller et al. |
| 9,289,539 B2 | 3/2016 | Wang |
| 2001/0002435 A1 | 5/2001 | Berg et al. |
| 2001/0018072 A1 | 8/2001 | Unger |
| 2001/0027299 A1 | 10/2001 | Yang et al. |
| 2001/0034363 A1 | 10/2001 | Li et al. |
| 2002/0002353 A1 | 1/2002 | Michal et al. |
| 2002/0010419 A1 | 1/2002 | Jayaraman |
| 2002/0039594 A1 | 4/2002 | Unger |
| 2002/0041896 A1 | 4/2002 | Straub et al. |
| 2002/0077684 A1 | 6/2002 | Clemens et al. |
| 2002/0082552 A1 | 6/2002 | Ding et al. |
| 2002/0095114 A1 | 7/2002 | Palasis |
| 2002/0098278 A1 | 7/2002 | Bates et al. |
| 2002/0099332 A1 | 7/2002 | Slepian et al. |
| 2002/0102280 A1 | 8/2002 | Anderson |
| 2002/0138048 A1 | 9/2002 | Tuch |
| 2002/0151844 A1 | 10/2002 | Yang et al. |
| 2002/0183380 A1 | 12/2002 | Hunter |
| 2002/0192280 A1 | 12/2002 | Hunter et al. |
| 2003/0004209 A1 | 1/2003 | Hunter et al. |
| 2003/0008923 A1 | 1/2003 | Dukart et al. |
| 2003/0045587 A1 | 3/2003 | Anderson |
| 2003/0064965 A1 | 4/2003 | Richter |
| 2003/0065024 A1 | 4/2003 | Lambert et al. |
| 2003/0099711 A1 | 5/2003 | Meadows et al. |
| 2003/0100577 A1 | 5/2003 | Zhu et al. |
| 2003/0100886 A1 | 5/2003 | Segal et al. |
| 2003/0100887 A1 | 5/2003 | Scott et al. |
| 2003/0114477 A1 | 6/2003 | Zhu et al. |
| 2003/0114791 A1 | 6/2003 | Rosenthal et al. |
| 2003/0157032 A1 | 8/2003 | Cavaillon et al. |
| 2003/0157161 A1 | 8/2003 | Hunter et al. |
| 2003/0207936 A1 | 11/2003 | Chen |
| 2003/0207939 A1 | 11/2003 | Ishibuchi et al. |

(56) References Cited

U.S. PATENT DOCUMENTS

| | | |
|---|---|---|
| 2003/0216699 A1 | 11/2003 | Falotico |
| 2003/0235602 A1 | 12/2003 | Schwarz |
| 2004/0002755 A1 | 1/2004 | Fischell et al. |
| 2004/0018296 A1 | 1/2004 | Castro et al. |
| 2004/0037886 A1 | 2/2004 | Hsu |
| 2004/0062810 A1 | 4/2004 | Hunter et al. |
| 2004/0073284 A1 | 4/2004 | Bates et al. |
| 2004/0076672 A1 | 4/2004 | Hunter et al. |
| 2004/0077677 A1 | 4/2004 | Ashraf et al. |
| 2004/0087902 A1 | 5/2004 | Richter |
| 2004/0097485 A1 | 5/2004 | Burkitt et al. |
| 2004/0127551 A1 | 7/2004 | Zhang et al. |
| 2004/0156816 A1 | 8/2004 | Anderson |
| 2004/0167152 A1 | 8/2004 | Rubino et al. |
| 2004/0176339 A1 | 9/2004 | Sherman et al. |
| 2004/0197408 A1 | 10/2004 | Gravett |
| 2004/0201117 A1 | 10/2004 | Anderson |
| 2004/0202712 A1 | 10/2004 | Lambert et al. |
| 2004/0204750 A1 | 10/2004 | Dinh |
| 2004/0219214 A1 | 11/2004 | Gravett et al. |
| 2004/0224001 A1 | 11/2004 | Pacetti et al. |
| 2004/0224003 A1 | 11/2004 | Schultz |
| 2004/0225077 A1 | 11/2004 | Gravett et al. |
| 2004/0230176 A1 | 11/2004 | Shanahan et al. |
| 2004/0258662 A1 | 12/2004 | Gibbons, Jr. et al. |
| 2005/0010170 A1 | 1/2005 | Shanley et al. |
| 2005/0025802 A1 | 2/2005 | Richard et al. |
| 2005/0037048 A1 | 2/2005 | Song |
| 2005/0038409 A1 | 2/2005 | Segal et al. |
| 2005/0042268 A1 | 2/2005 | Aschkenasy et al. |
| 2005/0049271 A1 | 3/2005 | Benjamin et al. |
| 2005/0054978 A1 | 3/2005 | Segal et al. |
| 2005/0055078 A1 | 3/2005 | Campbell |
| 2005/0080477 A1 | 4/2005 | Sydney et al. |
| 2005/0100580 A1 | 5/2005 | Osborne et al. |
| 2005/0101522 A1 | 5/2005 | Speck et al. |
| 2005/0123582 A1 | 6/2005 | Sung et al. |
| 2005/0131448 A1 | 6/2005 | Scopton |
| 2005/0152983 A1 | 7/2005 | Ashraf et al. |
| 2005/0159704 A1 | 7/2005 | Scott et al. |
| 2005/0171596 A1 | 8/2005 | Furst et al. |
| 2005/0182361 A1 | 8/2005 | Lennox |
| 2005/0186244 A1 | 8/2005 | Hunter et al. |
| 2005/0191323 A1 | 9/2005 | Chen |
| 2005/0191333 A1 | 9/2005 | Hsu |
| 2005/0192210 A1 | 9/2005 | Rothbard et al. |
| 2005/0209664 A1 | 9/2005 | Hunter et al. |
| 2005/0222191 A1 | 10/2005 | Falotico et al. |
| 2005/0234086 A1 | 10/2005 | Gu et al. |
| 2005/0234087 A1 | 10/2005 | Gu et al. |
| 2005/0234234 A1 | 10/2005 | Gu et al. |
| 2005/0238584 A1 | 10/2005 | Annapragada et al. |
| 2005/0239178 A1 | 10/2005 | Ruppen et al. |
| 2005/0246009 A1 | 11/2005 | Toner et al. |
| 2005/0250672 A9 | 11/2005 | Speck et al. |
| 2005/0251249 A1 | 11/2005 | Sahatjian et al. |
| 2005/0256564 A1 | 11/2005 | Yang et al. |
| 2005/0272758 A1 | 12/2005 | Bayever et al. |
| 2005/0278021 A1 | 12/2005 | Bates et al. |
| 2005/0288481 A1 | 12/2005 | DesNoyer et al. |
| 2006/0015170 A1 | 1/2006 | Jones et al. |
| 2006/0020243 A1 | 1/2006 | Speck et al. |
| 2006/0020331 A1 | 1/2006 | Bates et al. |
| 2006/0040971 A1 | 2/2006 | Zhu et al. |
| 2006/0045901 A1 | 3/2006 | Weber |
| 2006/0051392 A1 | 3/2006 | Heruth et al. |
| 2006/0052744 A1 | 3/2006 | Weber |
| 2006/0067977 A1 | 3/2006 | Labrecque et al. |
| 2006/0094745 A1 | 5/2006 | Ruffolo |
| 2006/0112536 A1 | 6/2006 | Herweck et al. |
| 2006/0121117 A1 | 6/2006 | Hunter et al. |
| 2006/0121545 A1 | 6/2006 | Molnar-Kimber et al. |
| 2006/0122697 A1 | 6/2006 | Shanley et al. |
| 2006/0127445 A1 | 6/2006 | Hunter et al. |
| 2006/0135549 A1 | 6/2006 | Graziani et al. |
| 2006/0135550 A1 | 6/2006 | Graziani et al. |
| 2006/0165753 A1 | 7/2006 | Richard |
| 2006/0171985 A1 | 8/2006 | Richard et al. |
| 2006/0173528 A1 | 8/2006 | Feld et al. |
| 2006/0183766 A1 | 8/2006 | Boni et al. |
| 2006/0184236 A1 | 8/2006 | Jones et al. |
| 2006/0188543 A1 | 8/2006 | Feng |
| 2006/0199834 A1 | 9/2006 | Zhu |
| 2006/0199954 A1 | 9/2006 | Shaw et al. |
| 2006/0224237 A1 | 10/2006 | Furst et al. |
| 2006/0230476 A1 | 10/2006 | Atanasoska et al. |
| 2006/0240113 A1 | 10/2006 | Hunter et al. |
| 2006/0246109 A1 | 11/2006 | Hossainy et al. |
| 2006/0257444 A1 | 11/2006 | Tropsha et al. |
| 2006/0257445 A1 | 11/2006 | Tropsha et al. |
| 2006/0282114 A1 | 12/2006 | Barone |
| 2007/0003629 A1 | 1/2007 | Hunter et al. |
| 2007/0003630 A1 | 1/2007 | Hunter et al. |
| 2007/0020308 A1 | 1/2007 | Richard et al. |
| 2007/0020380 A1 | 1/2007 | Ding |
| 2007/0032694 A1 | 2/2007 | Dinkelborg et al. |
| 2007/0050010 A1 | 3/2007 | Bates et al. |
| 2007/0059434 A1 | 3/2007 | Roorda et al. |
| 2007/0065484 A1 | 3/2007 | Chudzik et al. |
| 2007/0073385 A1 | 3/2007 | Schaeffer et al. |
| 2007/0077347 A1 | 4/2007 | Richter |
| 2007/0078446 A1 | 4/2007 | Lavelle |
| 2007/0078513 A1 | 4/2007 | Campbell |
| 2007/0117925 A1 | 5/2007 | Strickler et al. |
| 2007/0128118 A1 | 6/2007 | Yu et al. |
| 2007/0142422 A1 | 6/2007 | Rubino et al. |
| 2007/0142772 A1 | 6/2007 | Deshmukh et al. |
| 2007/0142905 A1 | 6/2007 | Hezi-Yamit et al. |
| 2007/0150043 A1 | 6/2007 | Richter |
| 2007/0150047 A1 | 6/2007 | Ruane et al. |
| 2007/0161967 A1 | 7/2007 | Fischer et al. |
| 2007/0162103 A1 | 7/2007 | Case et al. |
| 2007/0167735 A1 | 7/2007 | Zhong et al. |
| 2007/0168012 A1 | 7/2007 | Ragheb et al. |
| 2007/0184083 A1 | 8/2007 | Coughlin |
| 2007/0190103 A1 | 8/2007 | Hossainy et al. |
| 2007/0191934 A1 | 8/2007 | Blakstvedt et al. |
| 2007/0198080 A1 | 8/2007 | Ding et al. |
| 2007/0207184 A1 | 9/2007 | Ruane et al. |
| 2007/0212386 A1 | 9/2007 | Patravale et al. |
| 2007/0212394 A1 | 9/2007 | Reyes et al. |
| 2007/0218246 A1 | 9/2007 | Ding |
| 2007/0219642 A1 | 9/2007 | Richter |
| 2007/0225799 A1 | 9/2007 | Doty |
| 2007/0237803 A1 | 10/2007 | Cheng et al. |
| 2007/0244284 A1 | 10/2007 | Cheng et al. |
| 2007/0244548 A1 | 10/2007 | Myers et al. |
| 2007/0264307 A1 | 11/2007 | Chen et al. |
| 2007/0265565 A1 | 11/2007 | Johnson |
| 2007/0276466 A1 | 11/2007 | Lavelle et al. |
| 2007/0282422 A1 | 12/2007 | Biggs et al. |
| 2007/0286814 A1 | 12/2007 | Sawant et al. |
| 2007/0298069 A1 | 12/2007 | Bucay-Couto et al. |
| 2008/0021385 A1 | 1/2008 | Barry et al. |
| 2008/0038307 A1 | 2/2008 | Hoffmann |
| 2008/0082552 A1 | 4/2008 | Krishnaswamy |
| 2008/0102033 A1 | 5/2008 | Speck et al. |
| 2008/0102034 A1 | 5/2008 | Speck et al. |
| 2008/0114331 A1 | 5/2008 | Holman et al. |
| 2008/0118544 A1 | 5/2008 | Wang |
| 2008/0140002 A1 | 6/2008 | Ramzipoor et al. |
| 2008/0175887 A1 | 7/2008 | Wang |
| 2008/0183282 A1 | 7/2008 | Yedgar |
| 2008/0194494 A1 | 8/2008 | Martinez et al. |
| 2008/0215137 A1 | 9/2008 | Epstein et al. |
| 2008/0233062 A1 | 9/2008 | Krishnan |
| 2008/0255508 A1 | 10/2008 | Wang |
| 2008/0255509 A1 | 10/2008 | Wang |
| 2008/0255510 A1 | 10/2008 | Wang |
| 2008/0255658 A1 | 10/2008 | Cook et al. |
| 2008/0262412 A1 | 10/2008 | Atanasoska et al. |
| 2008/0274159 A1 | 11/2008 | Schultz |
| 2008/0274266 A1 | 11/2008 | Davis et al. |
| 2008/0276935 A1 | 11/2008 | Wang |

(56) References Cited

U.S. PATENT DOCUMENTS

| | | |
|---|---|---|
| 2008/0317827 A1 | 12/2008 | Wright et al. |
| 2009/0010987 A1 | 1/2009 | Parker et al. |
| 2009/0011116 A1 | 1/2009 | Herweck et al. |
| 2009/0035390 A1 | 2/2009 | Modak et al. |
| 2009/0047414 A1 | 2/2009 | Corbeil et al. |
| 2009/0069883 A1 | 3/2009 | Ding et al. |
| 2009/0076448 A1 | 3/2009 | Consigny et al. |
| 2009/0098176 A1 | 4/2009 | Helmus et al. |
| 2009/0105686 A1 | 4/2009 | Snow et al. |
| 2009/0105687 A1 | 4/2009 | Deckman et al. |
| 2009/0136560 A1 | 5/2009 | Bates et al. |
| 2009/0181937 A1 | 7/2009 | Faucher et al. |
| 2009/0182273 A1 | 7/2009 | Johnson |
| 2009/0187144 A1 | 7/2009 | Jayaraman |
| 2009/0208552 A1 | 8/2009 | Faucher et al. |
| 2009/0215882 A1 | 8/2009 | Bouzada et al. |
| 2009/0227948 A1 | 9/2009 | Chen et al. |
| 2009/0227949 A1 | 9/2009 | Knapp et al. |
| 2009/0238854 A1 | 9/2009 | Pacetti et al. |
| 2009/0246252 A1 | 10/2009 | Arps et al. |
| 2009/0324682 A1 | 12/2009 | Popowski |
| 2010/0030183 A1 | 2/2010 | Toner et al. |
| 2010/0055294 A1 | 3/2010 | Wang et al. |
| 2010/0063570 A1 | 3/2010 | Pacetti et al. |
| 2010/0068170 A1 | 3/2010 | Michal et al. |
| 2010/0068238 A1 | 3/2010 | Managoli |
| 2010/0069838 A1 | 3/2010 | Weber et al. |
| 2010/0069879 A1 | 3/2010 | Michal et al. |
| 2010/0081992 A1 | 4/2010 | Ehrenreich et al. |
| 2010/0087783 A1 | 4/2010 | Weber et al. |
| 2010/0179475 A1 | 7/2010 | Hoffmann et al. |
| 2010/0198150 A1 | 8/2010 | Michal et al. |
| 2010/0198190 A1 | 8/2010 | Michal et al. |
| 2010/0209472 A1 | 8/2010 | Wang |
| 2010/0272773 A1 | 10/2010 | Kangas et al. |
| 2010/0285085 A1 | 11/2010 | Stankus et al. |
| 2010/0324645 A1 | 12/2010 | Stankus et al. |
| 2010/0331816 A1 | 12/2010 | Dadino et al. |
| 2011/0054396 A1 | 3/2011 | Kangas et al. |
| 2011/0060275 A1 | 3/2011 | Christiansen |
| 2011/0129514 A1 | 6/2011 | Hossainy et al. |
| 2011/0137243 A1 | 6/2011 | Hossainy et al. |
| 2011/0143014 A1 | 6/2011 | Stankus et al. |
| 2011/0144577 A1 | 6/2011 | Stankus et al. |
| 2011/0144578 A1 | 6/2011 | Pacetti et al. |
| 2011/0152906 A1 | 6/2011 | Escudero et al. |
| 2011/0152907 A1 | 6/2011 | Escudero et al. |
| 2011/0159169 A1 | 6/2011 | Wang |
| 2011/0160658 A1 | 6/2011 | Wang |
| 2011/0160660 A1 | 6/2011 | Wang |
| 2011/0166548 A1 | 7/2011 | Wang |
| 2011/0178503 A1 | 7/2011 | Kangas |
| 2011/0190863 A1 | 8/2011 | Ostroot et al. |
| 2012/0029426 A1 | 2/2012 | Wang |
| 2012/0035530 A1 | 2/2012 | Wang |
| 2012/0143132 A1 | 6/2012 | Orlowski |
| 2013/0189190 A1 | 7/2013 | Wang |
| 2013/0189329 A1 | 7/2013 | Wang |
| 2013/0197431 A1 | 8/2013 | Wang |
| 2013/0197434 A1 | 8/2013 | Wang |
| 2013/0197435 A1 | 8/2013 | Wang |
| 2013/0197436 A1 | 8/2013 | Wang |
| 2013/0261603 A1 | 10/2013 | Wang |

FOREIGN PATENT DOCUMENTS

| | | |
|---|---|---|
| CN | 101264347 A | 9/2008 |
| DE | 10115740 A1 | 10/2002 |
| EP | 1118325 A2 | 7/2001 |
| EP | 1270018 A1 | 1/2003 |
| EP | 132737 A2 | 1/2004 |
| EP | 1539267 A2 | 6/2005 |
| EP | 1649853 A3 | 11/2006 |
| EP | 1666071 B1 | 8/2007 |
| EP | 1666070 B1 | 9/2007 |
| EP | 1857127 A1 | 11/2007 |
| EP | 1539266 B1 | 4/2008 |
| EP | 1913962 A1 | 4/2008 |
| EP | 1510220 B1 | 7/2008 |
| EP | 2123312 A2 | 11/2009 |
| EP | 1576970 B1 | 3/2010 |
| EP | 1669092 B1 | 3/2010 |
| EP | 1970185 A3 | 11/2010 |
| EP | 1586338 B1 | 1/2011 |
| EP | 2272550 A2 | 1/2011 |
| EP | 2127617 A4 | 9/2011 |
| EP | 1468660 B1 | 12/2011 |
| JP | 2002501788 A | 1/2002 |
| JP | 2003533286 A | 11/2003 |
| WO | 9843618 A2 | 10/1998 |
| WO | 0187368 A1 | 11/2001 |
| WO | 2002094179 A3 | 11/2002 |
| WO | 2004006976 A1 | 1/2004 |
| WO | 2004026357 A1 | 4/2004 |
| WO | 2004028582 A1 | 4/2004 |
| WO | 2004028610 A3 | 6/2004 |
| WO | 2004089291 A2 | 10/2004 |
| WO | 2005011769 A3 | 4/2005 |
| WO | 2006023859 A1 | 3/2006 |
| WO | 2006039634 A2 | 4/2006 |
| WO | 2006056984 A2 | 6/2006 |
| WO | 2006101573 A1 | 9/2006 |
| WO | 2006124647 A1 | 11/2006 |
| WO | 2006081210 A3 | 2/2007 |
| WO | 2007061529 A1 | 5/2007 |
| WO | 2007047416 A3 | 11/2007 |
| WO | 2007137298 A2 | 11/2007 |
| WO | 2007079560 A3 | 12/2007 |
| WO | 2007134239 A3 | 1/2008 |
| WO | 2007149161 A3 | 4/2008 |
| WO | 2008114585 A1 | 9/2008 |
| WO | 2007139931 A3 | 10/2008 |
| WO | 2008063576 A3 | 2/2009 |
| WO | 2009018816 A2 | 2/2009 |
| WO | 2008003298 A3 | 7/2009 |
| WO | 2008086794 A3 | 1/2010 |
| WO | 2010009335 A1 | 1/2010 |
| WO | 2016015874 A1 | 2/2016 |

OTHER PUBLICATIONS

Snell, Airway Bypass Stenting for Severe Emphysema, Apr. 2006, CTSNet, www.ctsnet.org/article/airway-bypass-stenting-severe-emphysema.

Sylvia S.W. Ng, William D. Figg, Alex Sparreboom; Taxane-Mediated Antiangiogenesis in Vitro: Influence of Formulation Vehicles and Binding Proteins; Cancer Research; Feb. 1, 2004; pp. 821-824.

"Scheller et al., Treatment of Coronary In-Stent Restenosis with a Paclitaxei-Coated Balloon Catheter; The New England Journal of Medicine; Nov. 16, 2006; pp. 2113-2124."

Scheller et al., Prevention of restenosis: is angioplasty the answer? Heart Journal, 2007; vol. 93; No. 5; pp. 539-541.

Terwogt et al.; "Alternative formulations of paclitaxel," Cancer Treatment Reviews (1997); 23: 87-95.

Chiang et al., "Potent inhibition of tumor survival in vivo by JI-lapachone plus taxol: Combining drugs imposes different artificial checkpoints," PNAS, vol. 96, No. 23, Nov. 9, 1999, at pp. 13369-13374.

New England Journal of Medicine, 1995, 332: 1004-1014.

Rowinsky, E. K., et al., "Drug therapy: paclitaxel (taxol)", Review Article, N Engl J Med, vol. 332, No. 15, pp. 1004-1014, (1995).

PPD "Evaluation of Butanol-Buffer Distribution Properties of C6-Ceraminde" PPD Project No. 7557-001, Aug. 20, 2008, pp. 1-14.

Prashant N. Chhajed et al., "Patterns of Pulmonary Complications Associated with Sirolimus," Respiration: International Review of Thoracic Diseases, vol. 73, No. 3, Mar. 2006, at pp. 367-374.

Sangster, James, "Octanoi-Water Partition Coefficients: Fundamentals and Physical Chemistry", Wiley Series in Solution Chemistry vol. 2, Chichester: John Wiley & Sons, vol. 2, Chapter 1 {1997).

(56) References Cited

OTHER PUBLICATIONS

Scheller et al., Paclitaxel Balloon Coating, a Novel Method for Prevention and Therapy of Restenosis, Circulation 2004;110; 810-814; originally published online Aug. 9, 2004.
Seymour R Halpin SF et al., "Corticosteroid prophylaxis for patients with increased risk of adverse reactions to Intravascular contrast agents: a survey of current practice in the UK," Department of Radiology, University Hospital of Nales, Heath Park, Cardiff, Clinical Radiology (1994), 49, pp. 791-795.
Toshimitsu Konno, M.D., et al., "Selective targeting of anti-cancer drug and simultaneous imaging enhancement in Solid tumors by arterially administered lipid contrast medium," Cancer 54:2367-2374, 1984.
Yushmanov, et al., "Dipyridamole Interacts with the Polar Part of Cationic Reversed Micelles in Chloroform: 1 H NMR and ESR Evidence", J. Colloid Interface Sci., vol. 191{2}, pp. 384-390 (1997).
Baumbach et al., "Local Drug Delivery: Impact of Pressure Substance Characteristics, and Stenting on Drug Transfer Into the Arterial Wall," Catheterization and Cardiovascular Interventions, vol. 47, pp. 102-106 (1999).
Charles et al., "Ceramide-Coated Balloon Catheters Limit Neointimal Hyperplasia After Stretch Injury in Carotid Arteries," Circulation Research published by the American Heart Association, 87, pp. 282-288 (2000).
Chun Li, et al, "Synthesis, Biodistribution and Imaging Properties of Indium-111-DTPA-Paclitaxel in Mice Bearing Mammary Tumors," The Journal of Nuclear Medicine, vol. 38, No. 7, Jul. 1997, 1042-1047.
Creel, C.J., et al., "Arterial Paclitaxel Distribution and Deposition", Circ Res, vol. 86, pp. 879-884 (2000).
D. M. Long et al., "Perfturocarbon Compounds as X-Ray Contrast Media in the Lungs," Bulletin de la Societe Internationale De Chirurgie, vol. 2, 1975, 137-141.
D.M. Jackson et al., "Current usage of contract agents, anticoagulant and antiplatelet drugs in angiography and angioplasty in the UK," Department of Diagnostic Radiology, Hammersmith Hospital, London, UK, Clinical Radiology (1995), 50, pp. 699-704.
Gyula Ostoros et al., "Fatal Pulmonary Fibrosis Induced Paclitaxel: A Case Report and Review of the Literature," International Journal of Gynecological Cancer, vol. 16, Suppl. 1, Jan. 2006, at pp. 391-393.
Gyula Ostoros et al., "PaclitaxelInduced Pulmonary Fibrosis," Lung Cancer, Elsevier, Amsterdam, NL, vol. 41, Aug. 1, 2003, at p. S280.
Herdeg et al., "Paclitaxel: Ein Chemotherapeuticum zum Restenoseprophylaxe? Experimentell Untersuchungen in vitr and in vivo," Z Kardiol, vol. 89 (2000) pp. 390-397.
Hershberger et al "Calcitriol (1, 25-dihydroxy cholecalciferol) Enhances Paclitaxel Antitumor Activity in Vitro and in Vivo and Accelerates Paclitaxel-Induced Apoptosis," Clin. Can. Res. 7: 1043-1051 (Apr. 2001).
International Search Report for International Application No. PCT/US2007/024116, dated Nov. 20, 2008.
International Search Report for International Application No. PCT/US2007/024108, dated Aug. 7, 2008.
International Search Report for International Application No. PCT/US2008/006415, dated May 20, 2008.
International Search Report for International Application No. PCT/US2008/006348, dated May 16, 2008.
International Search Report for International Application No. PCT/US2008/006417, dated May 20, 2008.
International Search Report for International Application No. PCT/US2008/007177, dated Sep. 16, 2008.
International Search Report for International Application No. PCT/US2008/007177, dated Dec. 2, 2008.
International Search Report for International Application No. PCT/US2008/006348, dated Nov. 26, 2008.
International Search Report for International Application No. PCT/US2008/006348, dated Jan. 28, 2009.
International Search Report for International Application No. PCT/US2008/006415, dated Nov. 24, 2008.
International Search Report for International Application No. PCT/US2008/006417, dated Nov. 24, 2008.
International Search Report for International Application No. PCT/US2009/004868, dated Jan. 4, 2010.
International Search Report for International Application No. PCT/US2009/004868, dated Jan. 1, 2010.
International Search Report for International Application No. PCT/US2009/004868, dated May 21, 2010.
International Search Report for International Application No. PCT/US2010/028599, dated Dec. 21, 2010.
J.F. Mitchel et al., ""Inhibition of Platelet Deposition and Lysis of Intracoronary Thrombus During Balloon AngioplastyUsing Urokinase-Coated Hydrogel Balloons"" Circulation 90, (Oct. 1994), pp. 1979-1988.
J. H. Baron, et al., "In vitro evaluation of c7E3-Fab {ReoPro} eluting polymer-coated coronary stents_" Cardiovascular Research, 46 {2000) pp. 585-594.
"Literature Alerts", Journal of Microencapsulation, vol. 17, No. 6, pp. 789-799 (2000).
K. Kandarpa et al., "Mural Delivery of Iloprost with Use of Hydrogel-coated Balloon Catheters Suppresses Local Platelet Aggregation" J. Vase Interv Radial 8, pp. 997-1004, Nov./Dec. 1997.
Kandarpa et al., "Site-specific Delivery of Iloprost during Experimental Angioplasty Suppresses Smooth Muscle Cell Proliferation" J. Vase Interv Radiol. 9, pp. 487-493, (1998).
Ken Iwai, et al., "Use of oily contrast medium for selective drug targeting to tumor: Enhanced therapeutic effect and X-ray image," Cancer Research, 44, 2115-2121, May 1994.
Laure Champion et al., "Brief Communication: Sirolimus-Associated Pneumonitis: 24 Cases in Renal Transplant Recipients," Annals of Internal Medicine, vol. 144, No. 7, Apr. 4, 2006, at pp. 505-509.
Leo, A, et al., "Partition coefficients and their uses" Chern Rev, vol. 71 (6), pp. 525-537 (1971).
Merriam-Webster, obtained online at: https://www.meriam-webster.com/dictionary/oligomer. Downloaded on Aug. 5, 2018. (Year: 2018).
Dictionary.com, obtained online at https://www.dictionary.com/browse/oligomer, Downloaded on Aug. 6, 2018. (Year: 2018).
European Search Report for EP09156858, dated Jul. 21, 2009.
Non-Final Office Action dated Mar. 13, 2019 pertaining to U.S. Appl. No. 15/674,144.
Non-Final Office Action dated Aug. 13, 2018 pertaining to U.S. Appl. No. 15/654,226.
Final Office Action dated Dec. 13, 2018 pertaining to U.S. Appl. No. 15/654,226.
Advisory Action dated Feb. 21, 2019 pertaining to U.S. Appl. No. 15/654,226.
European Search Report for EP09160605, dated Jul. 20, 2009.
European Search Report for EP10168411, dated Nov. 30, 2010.
European Search Report for EP10168412, dated Nov. 30, 2010.
European Search Report for EP10189393, dated Apr. 4, 2011.
Extended European Search Report pertaining to EP18169026.4 dated Jul. 13, 2018.
Office Action pertianing to corresponding U.S. Appl. No. 15/617,786 dated Jan. 10, 2019.
Office Action pertianing to corresponding U.S. Appl. No. 15/907,422 dated Dec. 20, 2018.
Malvern Panalytical, Polyolefin—We explain Polyolefins for you (accessed Nov. 29, 2018) pp. 1-5 (Year: 2018).
PMC Isochem, Vitamin E TPGS, NF and Food Grade, Feb. 2018.

DRUG RELEASING COATINGS FOR BALLOON CATHETERS

CROSS-REFERENCES TO RELATED APPLICATIONS

This application is a continuation of U.S. application Ser. No. 15/154,669, filed May 13, 2016, which is a continuation-in-part of U.S. application Ser. No. 15/067,739, filed Mar. 11, 2016, which is a continuation of U.S. application Ser. No. 14/683,612 filed Apr. 10, 2015, now U.S. Pat. No. 9,289,539, issued Mar. 22, 2016, which is a continuation of U.S. application Ser. No. 13/846,143, filed Mar. 18, 2013, now U.S. Pat. No. 9,005,161, issued Apr. 14, 2015, which is a continuation of U.S. application Ser. No. 12/731,835, filed Mar. 25, 2010, now U.S. Pat. No. 8,414,910, issued Apr. 9, 2013, which is a continuation-in-part of U.S. application Ser. No. 12/121,986, filed May 16, 2008, now U.S. Pat. No. 8,414,525, issued Apr. 9, 2013, which is a continuation-in-part of U.S. application Ser. No. 11/942,452, filed Nov. 19, 2007, now U.S. Pat. No. 8,414,909, issued Apr. 9, 2013, which claims the benefit of priority of U.S. Provisional Application No. 60/860,084, filed Nov. 20, 2006, of U.S. Provisional Application No. 60/880,742, filed Jan. 17, 2007, of U.S. Provisional Application No. 60/897,427, filed Jan. 25, 2007, of U.S. Provisional Application No. 60/903,529, filed Feb. 26, 2007, of U.S. Provisional Application No. 60/904,473, filed Mar. 2, 2007, of U.S. Provisional Application No. 60/926,850, filed Apr. 30, 2007, of U.S. Provisional Application No. 60/981,380, filed Oct. 19, 2007, and of U.S. Provisional Application No. 60/981,384, filed Oct. 19, 2007; application Ser. No. 15/154,669 being also a continuation-in-part of U.S. application Ser. No. 14/932,033, filed Nov. 4, 2015, which is a continuation of U.S. application Ser. No. 13/846,358, filed Mar. 18, 2013, now U.S. Pat. No. 9,180,485, issued Nov. 10, 2015, which is a continuation of U.S. application Ser. No. 12/549,180, filed Aug. 27, 2009, now U.S. Pat. No. 8,430,055, issued Apr. 30, 2013, which claims the benefit of priority of U.S. Provisional Application No. 61/092,872, filed Aug. 29, 2008. The full disclosures of all of the foregoing applications are incorporated by reference herein.

TECHNICAL FIELD

The present disclosure relates to balloon catheters, methods of preparing balloon catheters, and uses of balloon catheters. More specifically, the present disclosure relates to balloon catheters for delivering a therapeutic agent to a blood vessel, wherein the balloon catheters have a coating layer having a hydrophobic therapeutic agent and a combination of additives.

BACKGROUND

It has become increasingly common to treat a variety of medical conditions by introducing a medical device into the vascular system or other lumen within a human. While such treatment initially appears successful, the initial success is often compromised by the recurrence of disease, such as stenosis (i.e., restenosis) after such treatment. Restenosis involves a physiological response to vascular injury caused by angioplasty. Over time, de-endothelization and injury to smooth muscle cells results in thrombus deposition, leukocyte and macrophage infiltration, smooth muscle cell proliferation/migration, fibrosis, and extracellular matrix deposition. In response to the incidence of restenosis, numerous local drug delivery systems have been developed for the treatment restenosis after balloon angioplasty.

Balloon catheters are one such local delivery system that has been found to be effective in the treatment and prevention of restenosis. Generally, balloons coated with an active agent are pressed against the wall of a blood vessel when the blood vessel is dilated to deliver the active agent. Accordingly, it may be advantageous for the active agent in the coating to be rapidly released and absorbed by blood vessel tissues. Any component in the coating which inhibits rapid release of the active agent may be disadvantageous.

The iodine contrast agent iopromide has been used with paclitaxel to coat balloon catheters and has met some success in the treatment of restenosis. While it has been reported that such contrast agent improves adhesion of paclitaxel to the balloon surface, iodinated contrast agents suffer from a variety of disadvantages. For example, when used for diagnostic procedures, iodinated contrast agents have complication rates of 5-30%. Additionally, iodinated contrast agents are associated with the risk of bradycardia, ventricular arrthymia, and fibrillation, and may also induce renal failure. Further, the Food and Drug Administration issued a second public health advisory in 2006 concerning a serious late adverse reaction to contrast agents known as Nephrogenic Systemic Fibrosis or Mephrogenic Fibrosing Dermopathy.

Moreover, iodinated X-ray contrast agents are unable to cross membrane lipid bilayers in order to enter cells of the vasculature. As a result, they are not optimally effective at carrying hydrophobic therapeutic agents such as paclitaxel into cells. The percentage of paclitaxel reported to be taken up by vascular tissue after deployment of these devices is only 5-20%. Additionally, the compatibility and/or miscibility of paclitaxel and iopromide is not optimal, and the integrity and uniformity of coating is poor. Such deficiencies adversely affect the amount and uniformity of hydrophobic therapeutic agent delivered to target tissue. Accordingly, additional embodiments of coating layers for balloon catheters are desired.

SUMMARY

In one embodiment, a balloon catheter for delivering a therapeutic agent to a blood vessel is disclosed. The balloon catheter delivers a therapeutic agent to the blood vessel while the balloon catheter is deployed at a target site of the blood vessel. The balloon catheter includes an elongate member, an expandable balloon, and a coating layer. The elongate member has a lumen and a distal end. The expandable balloon is attached to the distal end of the elongate member and is in fluid communication with the lumen of the elongate member. The coating layer overlies an exterior surface of the expandable balloon. The coating layer includes a total drug load of a hydrophobic therapeutic agent and a combination of additives including a first additive and a second additive. The hydrophobic therapeutic agent is one of paclitaxel, rapamycin, or combinations thereof. The first additive is one of PEG sorbitan monolaurates, PEG sorbitan monooleates, or combinations thereof. The second additive is one of sorbitol, sorbitan, xylitol, gluconolactone, lactobionic acid, or combinations thereof.

In another embodiment, a balloon catheter for delivering a therapeutic agent to a blood vessel is disclosed. The balloon catheter delivers a therapeutic agent to the blood vessel while the balloon catheter is deployed at a target site of the blood vessel. In this embodiment, the balloon catheter includes an elongate member, an expandable balloon, and a coating layer. The elongate member has a lumen and a distal end. The expandable balloon is attached to the distal end of the elongate member and is in fluid communication with the lumen of the elongate member. The coating layer overlies an exterior surface of the expandable balloon. In this embodiment, the coating layer includes a total drug load of a hydrophobic therapeutic agent and a combination of additives including a first additive and a second additive. The total drug load of the hydrophobic therapeutic agent is from 2.5 µg to 6 µg per square millimeter of the expandable balloon. The hydrophobic therapeutic agent is one of paclitaxel, rapamycin, or combinations thereof. The first additive is one of PEG-20 sorbitan monolaurate, PEG-20 sorbitan monooleate, or combinations thereof. The second additive is one of sorbitol, gluconolactone, or combinations thereof. The ratio by weight of the combination of additives in the coating layer to the hydrophobic therapeutic agent in the coating layer is about 10 to 0.5.

It is understood that both the foregoing general description and the following detailed description are exemplary and explanatory only and are not restrictive of the present disclosure as claimed.

Skilled artisans should appreciate that elements in the figures are illustrated for simplicity and clarity and are not necessarily drawn to scale. For example, the dimensions of some of the elements in the figures may be exaggerated relative to other elements, as well as conventional parts removed, to help to improve understanding of the various embodiments described herein.

DETAILED DESCRIPTION

Embodiments of the present disclosure relate to balloon catheters for delivering a therapeutic agent to a blood vessel. In one embodiment, the balloon catheter includes an elongate member, an expandable balloon, and a coating layer. Reference will now be made in detail to balloon catheters. More particularly, embodiments of the balloon catheter and, more specifically, the elongate member and the expandable balloon of the balloon catheter will now be described in detail with reference to FIG. 1. Thereafter, embodiments of the coating layer will be described in detail with reference to FIG. 2.

I. Balloon Catheters With Coating Layer

Figure 1:
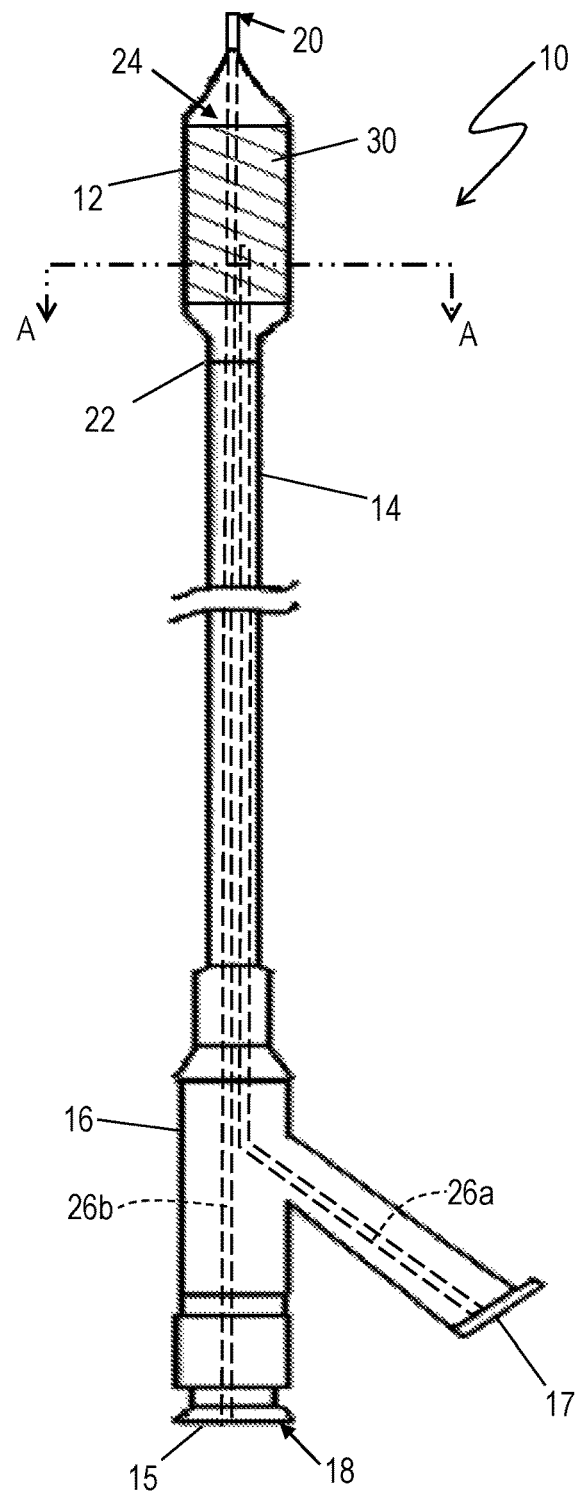
FIG. 1 is a perspective view of an exemplary embodiment of a balloon catheter according to the present disclosure.

Referring to FIG. 1, a balloon catheter 10 is disclosed. The balloon catheter 10 has a proximal end 18 and a distal end 20. The balloon catheter 10 may be any suitable catheter for desired use, including conventional balloon catheters known to one of ordinary skill in the art. For example, the balloon catheter 10 may be a rapid exchange or over-the-wire catheter. The balloon catheter 10 may be made of any suitable biocompatible material.

Figure 2:
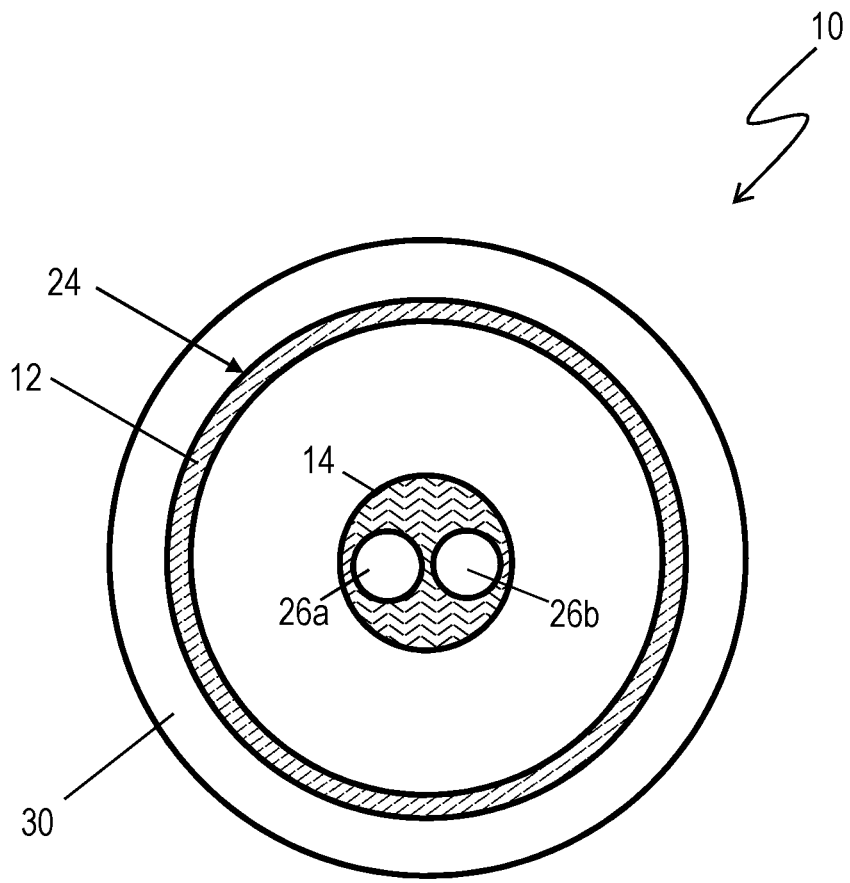
FIG. 2 is a cross-sectional view of an embodiment of the distal portion of the balloon catheter of FIG. 1, taken along line A-A, showing an exemplary coating layer.

As shown in FIGS. 1 and 2, in one embodiment, the balloon catheter 10 includes an expandable balloon 12 and an elongate member 14. The elongate member 14 extends between the proximal end 18 and the distal end 20 of the balloon catheter 10. The elongate member 14 has at least one lumen 26a, 26b and a distal end 22. The elongate member 14 may be a flexible member which is a tube made of suitable biocompatible material. The elongate member 14 may have one lumen or, as shown in FIGS. 1 and 2, more than one lumen 26a, 26b therein. For example, the elongate member 14 may include a guide-wire lumen 26b that extends to the distal end 20 of the balloon catheter 10 from a guide-wire port 15 at the proximal end 18 of the balloon catheter 10. The elongate member 14 may also include an inflation lumen 26a that extends from an inflation port 17 of the balloon catheter 10 to the inside of the expandable balloon 12 to enable inflation of the expandable balloon 12. From the embodiment of FIGS. 1 and 2, even though the inflation lumen 26a and the guide-wire lumen 26b are shown as side-by-side lumens, it should be understood that the one or more lumens present in the elongate member 14 may be configured in any manner suited to the intended purposes of the lumens including, for example, introducing inflation media and/or introducing a guide-wire. Many such configurations are well known in the art.

The expandable balloon 12 is attached to the distal end 22 of the elongate member 14. The expandable balloon 12 has an exterior surface 24 and is inflatable. The expandable balloon 12 is in fluidic communication with a lumen of the elongate member 14, (for example, with the inflation lumen 26a). At least one lumen of the elongate member 14 is configured to receive inflation media and to pass such media to the expandable balloon 12 for its expansion. Examples of inflation media include air, saline, and contrast media.

Still referring to FIG. 1, in one embodiment, the balloon catheter 10 includes a handle assembly such as a hub 16. The hub 16 may be attached to the balloon catheter 10 at the proximal end 18 of the balloon catheter 10. The hub 16 may connect to and/or receive one or more suitable medical devices, such as a source of inflation media or a guide wire. For example, a source of inflation media (not shown) may connect to the inflation port 17 of the hub 16 (for example, through the inflation lumen 26a), and a guide wire (not shown) may be introduced to the guide-wire port 15 of the hub 16, (for example through the guide-wire lumen 26b).

Referring now to FIG. 2, a balloon catheter 10 having a coating layer 30 is disclosed. The coating layer 30 overlies an exterior surface 24 of the expandable balloon 12. The coating layer 30 includes a hydrophobic therapeutic agent and a combination of additives. In one particular embodiment, the coating layer 30 consists essentially of the hydrophobic therapeutic agent and the combination of additives. Stated another way, in this particular embodiment, the coating layer 30 includes only the therapeutic agent and the combination of additives, without any other materially significant components. In another particular embodiment, the coating layer 30 is from about 0.1 µm to 15 µm thick.

A. Hydrophobic Therapeutic Agent

In one embodiment, the coating layer 30 includes a hydrophobic therapeutic agent. However, the coating layer 30 may also include two or more hydrophobic therapeutic agents. The hydrophobic therapeutic agent may be a lipophilic substantially water insoluble therapeutic agent. For example, the hydrophobic therapeutic agent may be paclitaxel, rapamycin, daunorubicin, doxorubicin, lapachone, vitamin D2, and vitamin D3. Additional suitable hydrophobic therapeutic agents generally include glucocorticoids (e.g., dexamethasone, betamethasone), hirudin, angiopeptin, aspirin, growth factors, antisense agents, polynucleotides, RNAi, siRNA, anti-cancer agents, anti-proliferative agents, oligonucleotides, and, more generally, anti-platelet agents, anti-coagulant agents, anti-mitotic agents, anti-metabolite agents, antioxidants, antiobiotic agents, anti-chemotactic, anti-inflammatory agents, photosensitizing agents, and collagen synthesis inhibitors.

With regard to antisense agents, polynucleotides, RNAi, and siRNA, suitable hydrophobic therapeutic agents include agents that inhibit inflammation and/or smooth muscle cell or fibroblast proliferation. With regard to anti-proliferative agents, suitable hydrophobic therapeutic agents include amlodipine and doxazosin. With regard to anti-platelet agents, suitable hydrophobic therapeutic agents include aspirin and dipyridamole. Aspirin may also be classified as an anti-platelet and an anti-inflammatory agent. Additionally, dipyridamole also exhibits anti-platelet characteristics. With regard to anti-coagulant agents, suitable hydrophobic therapeutic agents include heparin, protamine, hirudin, and tick anticoagulant protein.

With regard to anti-mitotic agents and anti-metabolite agents, suitable hydrophobic therapeutic agents include methotrexate, azathioprine, vincristine, vinblastine, 5-fluorouracil, adriamycin, and mutamycin. With regard to antioxidants, suitable hydrophobic therapeutic agents include probucol. With regard to antibiotic agents, suitable hydrophobic therapeutic agents include penicilin, cefoxitin, oxacillin, tobramycin, and gentamicin. With regard to photosensitizing agents, suitable hydrophobic therapeutic agents include agents for photodynamic or radiation therapy, including various porphyrin compounds such as porfimer. With regard to collagen synthesis inhibitors, suitable hydrophobic therapeutic agents include tranilast.

In one embodiment, the hydrophobic therapeutic agent includes at least one of paclitaxel, rapamycin, beta-lapachone, biologically active vitamin D, and combinations thereof. In one particular embodiment, the hydrophobic therapeutic agent is paclitaxel, rapamycin, or combinations thereof. In a further embodiment, the hydrophobic therapeutic agent is paclitaxel. Alternatively, in another further embodiment, the hydrophobic therapeutic agent is rapamycin.

In another embodiment, the hydrophobic therapeutic agent is provided as a total drug load in the coating layer 20. The total drug load of the hydrophobic therapeutic agent in the coating layer 30 may be from 1 µg to 20 µg, or alternatively from 2 µg to 10 µg, or alternatively from 2 µg to 6 µg, or alternatively from 2.5 µg to 6 µg per square millimeter of the expandable balloon 12. The hydrophobic therapeutic agent may also be uniformly distributed in the coating layer. Additionally, the hydrophobic therapeutic agent may be provided in a variety of physical states. For example, the hydrophobic therapeutic agent may be a molecular distribution, crystal form, or cluster form.

B. Combination of Additives

The coating layer 30 also includes a combination of additives. The combination of additives includes a first additive and a second additive. In one embodiment, the first additive is a surfactant and the second additive is a chemical compound having one or more hydroxyl, amino, carbonyl, carboxyl, acid, amide, or ester groups.

1. First Additive

In one embodiment, the first additive is a surfactant. However, the first additive may also include mixtures of surfactants. Such surfactants may be anionic, cationic, zwitterionic, or non-ionic. Examples of suitable non-ionic surfactants include polyethylene glycol fatty acids, polyethylene glycol fatty acid mono and diesters, polyethylene glycol glycerol fatty acid esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and derivatives thereof, polyethylene glycol alkyl phenols, polyoxyethylene-polyoxypropylene block copolymers, and sorbitan fatty acid esters. Examples of suitable ionic surfactants include quarternary ammonium salts, fatty acid salts, and bile salts.

With regard to polyethylene glycol (hereinafter "PEG") fatty acids, suitable hydrophilic surfactants include monoesters, esters of lauric acid, oleic acid, and stearic acid. Examples of such surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate, and PEG-20 oleate. With regard to PEG fatty acid diesters, suitable hydrophilic surfactants include PEG-20 dilaurate, PEG-20 dioleate, PEG-20 distearate, PEG-32 dilaurate, and PEG-32 dioleate. With regard to PEG fatty acids, suitable hydrophilic surfactants include PEG-20 glyceryl laurate, PEG-30 glyceryl laurate, PEG-40 glyceryl laurate, PEG-20 glyceryl oleate, and PEG-30 glyceryl oleate.

With regard to alcohol-oil transesterification products, suitable surfactants can be prepared by reaction of alcohol or polyalcohol with a variety of natural and/or hydrogenated oils. Examples of such alcohols include glycerol, propylene glycol, ethylene glycol, PEG, sorbitol, and pentaerythritol. Examples of such oils include castor oil, hydrogenated castor oil, corn oil, olive oil, peanut oil, palm kernel oil, apricot kernel oil, or almond oil. Examples of hydrophilic surfactants prepared by such reaction include PEG-35 castor oil, PEG-40 hydrogenated castor oil, PEG-25 trioleate, PEG-60 corn glycerides, PEG-60 almond oil, PEG-40 palm kernel oil, PEG-50 castor oil, PEG-50 hydrogenated castor oil, PEG-8 caprylic/capric glycerides, and PEG-6 caprylic/capric glycerides. Examples of hydrophobic surfactants prepared by such reaction include PEG-5 hydrogenated castor oil, PEG-7 hydrogenated castor oil, PEG-9 hydrogenated castor oil, PEG-6 corn oil, PEG-6 almond oil, PEG-6 apricot kernel oil, PEG-6 olive oil, PEG-6 peanut oil, PEG-6 hydrogenated palm kernel oil, PEG-6 palm kernel oil, PEG-6 triolein, PEG-8 corn oil, PEG-20 corn glycerides, and PEG-20 almond glycerides.

With regard to polyglyceryl fatty acids, suitable hydrophobic surfactants include polyglyceryl oleate, polyglyceryl-2 dioleate, polyglyceryl-10 trioleate, polyglyceryl oleate, polyglyceryl-2 diolate, polyglyceryl-10 trioleate, polyglyceryl stearate, polyglyceryl laurate, polyglyceryl myristate, polyglyceryl palmitate, and polyglyceryl linoleate. Suitable hydrophilic surfactants include polyglyceryl-10 laurate, polyglyceryl-10 oleate, and polyglyceryl-10 mono, diolate, polyglyceryl-10 stearate, polyglyceryl-10 linoleate, polyglyceryl-6 stearate, polyglyceryl-6 palmitate, and polyglyceryl-6 linoleate. Polyglyceryl polyricinoleates (i.e. polymuls) are also suitable surfactants.

With regard to propylene glycol fatty acid esters, suitable hydrophobic surfactants include propylene glycol monolaurate, propylene glycol ricinoleate, propylene glycol monooleate, propylene glycol dicaprylate/dicaprate, and propylene glycol dioctanoate. With regard to sterol and sterol derivatives, suitable surfactants include PEG derivatives such as PEG-24 cholesterol ether.

With regard to PEG sorbitan fatty acid esters, suitable surfactants include PEG sorbitan monolaurates, PEG sorbitan monopalmitates, PEG sorbitan monooleates, and PEG sorbitan monostearates. Examples of such surfactants include PEG-20 sorbitan monolaurate, PEG-20 sorbitan monopalmitate, PEG-20 sorbitan monooleate, and PEG-20 sorbitan monostearate. With regard to PEG alkyl ethers, suitable surfactants include PEG-3 oleyl ether and PEG-4 lauryl-ether.

With regard to sugars and derivatives thereof, suitable surfactants include sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyl-N-methylglucamide, n-noyl-β-D-glucopyranoside, octanoyl-N-methylglucamide, n-octyl-β-D-glucopyranoside, and octyl-β-D-thioglucopyranoside. With regard to PEG alkyl phenols, suitable surfactants include PEG-10-100 nonyl phenol, PEG-15-100 octyl phenol ether, tyloxapol, octoxynol, and nonoxynol.

With regard to polyoxyethylene-polyoxypropylene (hereinafter "POE-POP") block copolymers, such block copolymers include hydrophilic polyoxyethylene and hydrophobic polyoxypropylene moieties having the formula HO $(C_2H_4O)_a(C_3H_6O)_b(C_2H_4O)_aH$ where "a" and "b" denote the number of polyoxyethylene and polyoxypropylene units, respectively. Such polymers are referred to as poloxamers. Suitable hydrophilic poloxamers include Poloxamers 108, 188, 217, 238, 288, 338, and 407. Suitable hydrophobic poloxamers include Poloxamers 124, 182, 183, 212, 313, and 335. With regard to sorbitan fatty acid esters, suitable hydrophobic surfactants include sorbitan monolaurate, sorbitan monopalmitate, sorbitan monooleate, and sorbitan monostearate.

With regard to ionic surfactants, suitable ionic surfactants include benzalkonium chloride, benzethonium chloride, cetylpyridinium chloride, docecyl trimethyl ammonium bromide, sodium docecylsulfates, dialkyl methylbenzyl ammonium chloride, edrophonium chloride, domiphen bromide, dialkylesters of sodium sulfonsuccinic acid, sodium dioctyl sulfosuccinate, sodium cholate, and sodium taurocholate.

Such surfactants are stable under heating and are capable of surviving an ethylene oxide sterilization process (which may be employed in preparing the balloon catheters). Moreover, such surfactants do not react with paclitaxel or rapamycin under the sterilization process. Additionally, such surfactants may protect the hydrophobic therapeutic agents from premature release during the device delivery process while facilitating rapid release and elution of the hydrophobic therapeutic agent.

In one embodiment, the surfactant is a PEG sorbitan monolaurate, a PEG sorbitan monooleate, or a combination thereof. In one particular embodiment, the surfactant is a PEG sorbitan monolaurate, and in a further embodiment, the surfactant is PEG-20 sorbitan monolaurate (i.e. Tween-20). In another particular embodiment, the surfactant is a PEG sorbitan monooleate, and in a further embodiment, the surfactant is PEG-20 sorbitan monooleate (i.e. Tween-80).

2. Second Additive

In one embodiment, the second additive is a chemical compound having one or more hydroxyl, amino, carbonyl, carboxyl, acid, amide, or ester groups. However, the second additive may also include mixtures of chemical compounds having one or more hydroxyl, amino, carbonyl, carboxyl, acid, amide or ester groups. The chemical compound has at least one hydroxyl group. The hydroxyl group is suitable as the hydrophilic moiety because it is unlikely to react with the hydrophobic therapeutic agent. In one particular embodiment, the chemical compound has a molecular weight less than 5,000-10,000, or alternatively less than 750-1,000, or alternatively less than 750. In a further embodiment, the chemical compound has a molecular weight of greater than 80. In an exemplary embodiment, the chemical compound has a molecular weight less than that of the hydrophobic therapeutic agent.

In one embodiment, the chemical compound has four or more hydroxyl groups. In one particular embodiment, the chemical compound having more than four hydroxyl groups has a melting point of 120° C. or less. In another particular embodiment, the chemical compound has three adjacent hydroxyl groups that in stereo configuration are all on one side of the molecule. Without being bound by the theory, it is believed that the stereo configuration of the three adjacent hydroxyl groups may enhance drug binding.

Large molecules diffuse slowly. If the molecular weight of the additive or the chemical compound is high, for example above 800, above 1000, above 1200, above 1500, or above 2000, the chemical compound may elute off of the exterior surface 24 of the expandable balloon 12 too slowly. For example, the hydrophobic therapeutic agent may be released in greater than two minutes. However, if the chemical compound has more than four hydroxyl groups it will have increased hydrophilic properties such that the hydrophobic therapeutic agent may elute off of the exterior surface 24 of the expandable balloon 12 quickly. For example, the hydrophobic therapeutic agent may be released at the target site in less than two minutes. Without being bound by the theory, it is believed that the increased hydrophilicity may play a role in: (1) aiding in the elution of the coating layer 30 off of the exterior surface 24 of the expandable balloon 12; (2) accelerating the release of the hydrophobic therapeutic agent; and (3) improving or facilitating the movement of the hydrophobic therapeutic agent through the water barriers and the polar head groups of lipid bilayers in cells membranes to penetrate tissues.

Examples of chemical compounds having one or more hydroxyl, amino, carbonyl, carboxyl, acid, amide, or ester moieties include amino alcohols, hydroxyl carboxylic acids, esters, and anhydrides, hydroxyl ketones, hydroxyl lactones, hydroxyl esters, sugar phosphates, sugar sulfate ethyl oxides, ethyl glycols, amino acids and salts thereof, peptides, proteins, sorbitan, glycerol, polyalcohols, phosphates, sulfates, organic acids, esters, salts, vitamins, and combinations of amino alcohols and organic acids.

With regard to amino acids and salts thereof, suitable chemical compounds include alanine, arginine, asparagines, aspartic acid, cysteine, cystine, glutamic acid, glutamine, glycine, histidine, proline, isoleucine, leucine, lysine, methionine, phenylalanine, serine, threonine, tryptophan, tyrosine, valine, and derivatives thereof. Additionally, amino acid dimers, sugar conjugates, and derivatives thereof may also be suitable chemical compounds. For example, catecholamines such as dopamine, levodopa, carbidoga, and DOPA may also be suitable chemical compounds.

With regard to peptides, oligopeptides and peptides are suitable as chemical compounds because hydrophobic and hydrophilic amino acids may be coupled to create various sequences of amino acids, facilitating permeation of tissue by the hydrophobic therapeutic agent. With regard to proteins, suitable chemical compounds include albumins, immunoglobulins, caseins, hemoglobins, lysozymes, immunoglobins, a-2-macroglobulin, fibronectins, vitronectins, firbinogens, and lipases. In an exemplary embodiment, the chemical compound is serum albumin. Such protein is suitable because it is water soluble and contains significant hydrophobic portions to bind the hydrophobic therapeutic agent.

With regard to vitamins, suitable chemical compounds include fat-soluble vitamins and salts thereof and water-soluble vitamins and amphiphilic derivatives thereof. Suitable examples of fat-soluble vitamins and salts thereof include alpha-tocopherol, beta-tocopherol, gamma-tocopherol, delta-tocopherol, tocopherol acetate, ergosterol, 1-alpha-hydroxycholecal-ciferol, vitamin D2, vitamin D3, alpha-carotene, beta-carotene, gamma-carotene, vitamin A, fursultiamine, methylolriboflavin, octotiamine, pro sultiamine, riboflavine, vintiamol, dihydrovitamin K1, menadiol diacetate, menadiol dibutyrate, menadiol disulfate, menadiol, vitamin K1, vitamin K1 oxide, vitamins K2, vitamin K-S(II), and folic acid in free acid form. Suitable examples of water-soluble vitamins and amphiphilic derivatives thereof include acetiamine, benfotiamine, pantothenic acid, cetotiamine, cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U.

With regard to organic acids, esters, and anhydrides, suitable chemical compounds include acetic acid and anhydride, benzoic acid and anhydride, diethylenetriaminepentaacetic acid dianhydride, ethylenediaminetetraacetic dianhydride, maleic acid and anhydride, succinic acid and anhydride, diglycolic anhydride, glutaric anhydride, ascorbic acid, citric acid, tartaric acid, lactic acid, oxalic acid, aspartic acid, nicotinic acid, 2-pyrrolidone-5-carboxylic acid, and 2-pyrrolidone.

With regard to amino alcohols, alcohols, amines, acids, amides, and hydroxyl acids, suitable chemical compounds include L-ascorbic acid and salts thereof, D-glucoascorbic acid and salts thereof, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactitol, sorbitol, glucitol, sugar phosphates, glucopyranose phosphate, sugar sulphates, sinapic acid, vanillic acid, vanillin, methyl paraben, propyl paraben, xylitol, 2-ethoxyethanol, sugars, galactose, glucose, ribose, mannose, xylose, sucrose, lactose, maltose, arabinose, lyxose, fructose, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and amine described above, polyglycidol, glycerols, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol, and penta(propylene glycol), poly(propylene glycol) oligomers, a block copolymer of PEG and polypropylene glycol, derivatives thereof, and combinations thereof.

Such chemical compounds are stable under heating and are capable of surviving an ethylene oxide sterilization process. Moreover, such chemical compounds do not react with paclitaxel or rapamycin under the sterlization process. In particular, without being bound by the theory, it is believed that hydroxyl, ester, and amide groups are unlikely to react with hydrophobic therapeutic agents such as paclitaxel or rapamycin. However, with specific regard to L-ascorbic acid and salts thereof as well as diethanolamine, such chemical compounds do not necessarily survive such sterilization processes and do react with paclitaxel. Additionally, in some instances, amine and acid groups (e.g., benzoic acid, gentisic acid, diethanolamine, and ascorbic acid) do react with hydrophobic therapeutic agents such as paclitaxel and may not be stable under ethylene oxide sterilization, heating, and aging processes. Accordingly, different sterilization methods should be employed with regard to such specific chemical compounds. Finally, while the chemical compounds described herein rapidly elute the hydrophobic therapeutic agent off of the expandable balloon 12 during deployment at the target site, absorption of the hydrophobic therapeutic agent by tissue is unexpectedly high. Such is particularly apparent with regard to hydroxyl lactones including ribonic acid lactone and gluconolactone.

In one embodiment, the chemical compound is sorbitol, sorbitan, xylitol, gluconolactone, lactobionic acid, or a combination thereof. In one particular embodiment, the chemical compound is sorbitol, gluconolactone, or combinations thereof. In a further embodiment, the chemical compound is sorbitol. Alternatively, in a further particular embodiment, the chemical compound is gluconolactone.

Additionally, the surfactants and combinations of surfactants described herein may also be employed in combination with the chemical compounds and combinations of chemical compounds described herein. For example, in one particular embodiment, the coating layer includes a hydrophobic therapeutic agent, a first additive, and a second additive, wherein the hydrophobic therapeutic agent is paclitaxel, the first additive is PEG-20 sorbitan monolaurate, PEG-20 sorbitan monooleate, or combinations thereof, and the second additive is one of sorbitol, gluconolactone, or combinations thereof. In another particular embodiment, the coating layer includes a hydrophobic therapeutic agent, a first additive, and a second additive, wherein the hydrophobic therapeutic agent is paclitaxel, the first additive is PEG-20 sorbitan monolaurate, and the second additive is sorbitol. In yet another particular embodiment, the coating layer includes a hydrophobic therapeutic agent, a first additive, and a second additive, wherein the hydrophobic therapeutic agent is paclitaxel, and the second additive is gluconolactone.

In one embodiment, the combination of additives in the coating layer 30 is from 1 µg to 20 µg. In another embodiment, the combination of additives and the hydrophobic therapeutic agent are provided in specific weight ratios in the coating layer 30. For example, the ratio by weight of the combination of additives in the coating layer 30 to the hydrophobic therapeutic agent in the coating layer 30 is about 20 to 0.05, or alternatively about 10 to 0.5, or alternatively about 5 to 0.8. Alternatively, in another embodiment, the ratio by weight of the hydrophobic therapeutic agent in the coating layer 30 to the combination of additives is about 0.5 to 3. In yet another embodiment, the balloon catheter 10 is capable of releasing the hydrophobic therapeutic agent and the combination of additives to the tissue in about 0.1 to 30 minutes, or alternatively in about 0.1 to 10 minutes, or alternatively in about 0.2 to 2 minutes, or alternatively in about 0.1 to 1 minute. Such timing of release refers to the timing during which the expandable balloon 12 is inflated and pressing the coating layer 30 into contact with the target tissue.

C. Solvents

The hydrophobic therapeutic agent is water insoluble. The combination of additives is soluble in aqueous solvent and polar organic solvent. Such aqueous solvent and polar organic solvents may be employed in preparing the coating layer. Suitable aqueous solvents include water. Suitable polar organic solvents include alkanes, aromatic solvents, alcohols, ethers, esters/acetates, ketones, and mixtures thereof.

With regard to alkanes, suitable solvents include hexane, octane, cyclohexane, and heptane. With regard to aromatic solvents, suitable solvents include benzene, toluene, and xylene. With regard to alcohols, suitable solvents include methanol, ethanol, propanol, and isopropanol, diethylamide, ethylene glycol monoethyl ether, trascutol, and benzyl alcohol. With regard to ethers, suitable solvents include dioxane, dimethyl ether and tetrahydrofuran. With regard to esters/acetates, suitable solvents include ethyl acetate and isobutyl acetate. With regard to ketones, suitable solvents include acetone, acetonitrile, diethyl ketone, and methyl ethyl ketone. Suitable solvents also include mixtures of aqueous solvents and polar organic solvents. For example, suitable mixtures of aqueous solvents and polar organic solvents may include water and ethanol, water and acetone, and water and methanol, water and tetrahydrofuran.

Embodiments of the balloon catheter have been described in detail. Further embodiments directed to methods of preparing balloon catheters will now be described.

II. Methods for Preparing Balloon Catheters

Methods for preparing a balloon catheter 10 may include (1) preparing a coating solution including a solvent, a therapeutic agent, and a combination of additives, (2) loading a metering dispenser with the coating solution, (3) inflating the balloon catheter 10 to 0 to 3 atm, and rotating the balloon catheter 10 about the longitudinal axis of the catheter and/or moving the balloon catheter 10 in a linear direction along the longitudinal or transverse axis of the balloon catheter 10, (4) dispensing the coating solution from the metering dispenser onto an exterior surface 24 of the balloon catheter 10 and flowing the coating solution on the surface of the balloon catheter 10 while the balloon catheter 10 is rotating and/or linearly moving, (5) evaporating the solvent, forming a coating layer 30 on the balloon catheter 10, (6) drying, folding, and wrapping the balloon catheter 10, and (7) sterilizing the balloon catheter 10. In one embodiment, the method for preparing the balloon catheter 10 further includes (8) drying the balloon catheter 10 after sterilization.

The coating solution includes a solvent, a hydrophobic therapeutic agent, and a combination of additives. In one particular embodiment, the coating solution consists essentially of the solvent, the hydrophobic therapeutic agent, and the combination of additives. The solvent, the hydrophobic therapeutic agent, and the combination of additives are as previously discussed. The content of the hydrophobic therapeutic agent in the coating solution can be from 0.5-50% by weight based on the total weight of the solution. The content of the combination of additives in the coating solution can be from 1-45% by weight, from 1 to 40% by weight, or from 1-15% by weight based on the total weight of the solution. The amount of solvent employed is dependent upon the coating process and viscosity.

In one particular embodiment, loading the metering dispenser with the coating solution, inflating the balloon catheter 10 to 0 atm to 3 atm, dispensing the coating solution from the metering dispenser, and evaporating the solvent, (as set forth in (2)-(5) above), occur concomitantly. In another embodiment, loading the metering dispenser with the coating solution, inflating the balloon catheter 10 to 0 atm to 3 atm, dispensing the coating solution from the metering dispenser, and evaporating the solvent, (as set forth in (2)-(5) above) are repeated until a therapeutically effective amount of the hydrophobic therapeutic agent in the coating solution is deposited on the exterior surface 24 of the balloon catheter 10.

A. Preparing a Coating Solution

With regard to preparing the coating solution, suitable techniques for preparing the coating solution include dispersing, dissolving, diffusing, or otherwise mixing the solvent, the hydrophobic therapeutic agent, and the combination of additives (as previously discussed). In one embodiment, the coating solution is prepared by mixing the solvent, the hydrophobic therapeutic agent, and the combination of additives together simultaneously.

Alternatively, in another embodiment, the coating solution may be prepared by adding the hydrophobic therapeutic agent and the combination of additives sequentially to the solvent. Such technique of sequentially adding components to the solvent may be based upon solubility of such components and/or other parameters known in the art. For example, the coating solution may be prepared by first adding the hydrophobic therapeutic agent to the solvent and then adding the combination of additives. Alternatively, the combination of additives may be added first to the solvent, after which the hydrophobic therapeutic agent may be added. Adding the combination of additives first to the solvent may be beneficial wherein a hydrophobic therapeutic does not sufficiently dissolve in a solvent (when added prior to the combination of additives). Without being bound by the theory, it is believed that the combination of additives will increase the solubility of the hydrophobic therapeutic agent in the solvent. In some embodiments, preparation of the coating solution may also involve homogenization under high shear conditions and optionally under pressure. In some embodiments, the preparation of the coating solution may also involve filtering the coating solution. For example, in one particular embodiment, the coating solution is prepared by: (1) mixing a fixed amount of the hydrophobic therapeutic agent, the combination of additives, and the solvent, (2) stirring the resulting mixture at room temperature, for example, or with slight heating such as to less than 60° C. until a homogenous solution is obtained, and (3) filtering the solution through a 0.45 µm filter.

Alternatively, in another embodiment, combinations of two or more solvents may be used, for example, by combining two solvents prior to addition of a hydrophobic therapeutic agent and a combination of additives. As another example, combinations of two or more solvents may be used by adding a hydrophobic therapeutic agent to one solvent and a combination of additives to another solvent and then combining. As still another example, combinations of two or more solvents may be used by adding only one of the hydrophobic therapeutic agent or the combination of additives to one solvent and then adding the second solvent and the remaining hydrophobic therapeutic agent or the combination of additives.

B. Loading a Metering Dispenser with the Coating Solution

With regard to loading a metering dispenser with the coating solution, suitable metering dispensers are as disclosed in U.S. Pub. No. 2010/0055294, the disclosure of which is incorporated by reference in its entirety. In one embodiment, the metering dispenser is a portion of an apparatus for coating a balloon catheter 10. The apparatus for coating a balloon catheter 10 may be semi-manual or automated. Briefly, in one embodiment, such apparatus includes an apparatus capable of rotating the balloon catheter 10 around its longitudinal axis and moving the balloon catheter 10 back and forth in the direction of its longitudinal or transverse axis, a controller coordinating the dispenser and the apparatus, and a coating solution storage container.

In one embodiment, the metering dispenser includes a dispensing tip connected to the metering dispenser for easy coating application. The dispensing tip may include a hub and a tip. In one particular embodiment, the hub is connected to the metering dispenser. The tip may be used to apply coating on the balloon catheter 10 either by contact or non-contact. The tip opening may have different shapes including, but not limited to, circular, oval, square, and rectangular. Additionally, the tip may be straight or with an angle (135°, 45° or 90°) and may be rigid or flexible. The tip may be tapered, non-tapered, Teflon-lined, Teflon-coated, and Teflon-lined and crimped or may be a brush. In one embodiment, the dispensing tip is made of metals, metal alloys, and a metal with a polymer coating or lining. For example, in one embodiment, the dispensing tip is made of stainless steel, polyethylene, polypropylene, polyesters, polyamides, polyurethanes, PTFE, metal with a PTFE coating or lining.

In another embodiment, the dispensing tip has an opening and a flexible tail. The flexible tail may be threaded through the tip opening of the dispensing tip or may be attached to the side of the tip. In embodiments, the flexible tail contacts the expandable balloon 12 to be coated. In some embodiments, the metering dispenser is a syringe, a syringe pump, a metering pipette, or an automatic metering system. In another embodiment, the automatic metering system includes a micro linear pump module, a dispensing controller module, a dispensing tip and other accessories from IVEK Corporation.

C. Inflating the Balloon Catheter

With regard to inflating the expandable balloon 12 of the balloon catheter 10, in one embodiment, the expandable balloon 12 is inflated from 0 atm to about 3 atm. Additionally, the balloon catheter 10 may be rotated about the longitudinal axis thereof and/or moved in a linear direction along the longitudinal or transverse axis thereof.

In one particular embodiment, the apparatus for coating the balloon catheter 10 concurrently rotates the balloon catheter 10 around its longitudinal axis at uniform rotational or tangential speed and translocates the balloon catheter 10 back and forth at uniform frequency in a longitudinal direction. More particularly, in this particular embodiment, the apparatus for coating the balloon catheter 10 moves the balloon catheter 10 linearly back and forth along a rail with uniform frequency while rotating the balloon catheter 10 at uniform rotational/tangential speed.

In an alternative embodiment, the metering dispenser moves linearly back and forth along a rail with uniform frequency while the apparatus capable of rotating the balloon catheter 10 rotates the balloon catheter 10 at uniform rotational/tangential speed.

D. Dispensing the Coating Solution from the Metering Dispenser onto an Exterior Surface 24 of the Balloon Catheter 10

With regard to dispensing the coating solution from the metering dispenser onto an exterior surface 24 of the balloon catheter 10, in one embodiment, the coating solution is dispensed from the metering dispenser while the balloon catheter 10 is rotating and/or linearly moving. During dispensing, the coating solution flows continuously to the exterior surface 24 of the balloon catheter 10 without forming droplets. In one embodiment, the drops of the coating solution move back and forth longitudinally and transversely over the exterior surface 24 of the balloon catheter 10 while the solvent evaporates, resulting in the consistent and uniform deposition of coating solution over the exterior surface 24 of the balloon catheter 10 and resulting in a uniform dry coating layer over the exterior surface 24 of the balloon catheter 10. Without being bound by the theory, it is believed that the rotational and traversal movements allow the flexible tail to break the surface tension between the coating and the expandable balloon 12, forming a uniform coating on the exterior surface 24 of the balloon catheter 10.

During dispensing, in one embodiment, the balloon catheter 10 and/or the dispensing tip of the metering dispenser move transversely and rotationally. In one particular embodiment, the rotation speed is from 0.1 to 10 revolutions per second, or alternatively from 0.5 to 5 revolutions per second, or alternatively from 0.8 to 2 revolutions per second. The linear or transverse speed is from 0.1 mm per second to 100 mm per second, or alternatively from 1 mm per second to 75 mm per second, or from 2 mm per second to 50 mm per second. The dispensing time is from 2 seconds to 300 seconds, or alternatively from 5 seconds to 120 second. The dispensing time is dependent upon the dispensing coating volume and diameters and lengths of the balloon catheter 10.

E. Evaporating the Solvent Forming a Coating Layer 30 on the Balloon Catheter 10

With regard to evaporating the solvent, in one embodiment, the solvent is evaporated while the coating solution is moving at a uniform speed. Without being bound by the theory, it is believed that such technique forms a substantially uniform dry coating layer 30 on the exterior surface 24 of the balloon catheter 10. In one particular embodiment, the apparatus for coating the balloon catheter 10 includes a fan for accelerating solvent evaporation.

F. Drying, Folding, and Wrapping the Balloon Catheter 10

With regard to drying, folding, and wrapping the balloon catheter 10, the coating solution may solidify on the exterior surface 24 of the balloon catheter 10 during the transverse and rotational motion of the balloon catheter 10. In one embodiment, the time of solidifying of the coating layer 30 on the expandable balloon 12 after dispensing of the liquid coating is from 0.1 minutes to 10 minutes, or alternatively from 0.5 minutes to 5 minutes. Following solidification, in one embodiment, the coated balloon catheter 10 is dried at room temperature for 12 hours to 24 hours.

The expandable balloon 12 may be folded after drying. Upon folding, the dried and folded balloon catheter 10 is rewrapped. Additionally, in one particular embodiment, a properly sized balloon protector is placed upon the wrapped balloon catheter 10 and the balloon catheter 10 is packaged.

G. Sterilizing the Balloon Catheter 10

With regard to sterilizing the balloon catheter 10, suitable sterilization techniques may include, but should not be limited to, sterilization with ethylene oxide and sterilization with an electron beam. In one particular embodiment, the balloon catheter 10 is sterilized with ethylene oxide.

H. Drying the Balloon Catheter 10 After Sterilization

After sterilizing the balloon catheter 10, in one embodiment, the balloon catheter 10 is dried. More particularly, in one embodiment, the balloon catheter 10 is dried under vacuum at about 0° C. to 100° C. for approximately 2 hours to 56 hours. In another embodiment, the balloon catheter 10 is dried under vacuum at about 5° C. to about 45° C. Without being bound by the theory, it is believed that the drying process improves integrity of the coating layer 30, protects loss of coating components during transit through body passages to the target treatment site, and improves drug absorption in the tissue.

I. Optional Post Treatment with DMSO

After depositing the coating layer 30 on the balloon catheter 10, in one embodiment, DMSO or other solvent is applied to the surface of the coating layer 20. The DMSO or other solvent may be applied to the surface by dipping, spraying, or any other suitable method known in the art. DMSO readily dissolves hydrophobic therapeutic agents and penetrates the membranes of target cells. DMSO may also enhance tissue absorption. More particularly, without being bound by the theory, it is believed that DMSO displaces water from the lipid head groups and protein domains of the lipid bilayer of the cell membrane of target cells, which indirectly loosens the lipid structure and accelerates absorption and penetration of the hydrophobic therapeutic agent.

Embodiments of the preparation of balloon catheters have been described in detail. Further embodiments directed to uses of balloon catheters will now be described.

III. Uses of Balloon Catheters

Uses of the balloon catheters as previously discussed are disclosed. Generally, the balloon catheter 10 is employed to deliver a hydrophobic therapeutic agent to a blood vessel while the balloon catheter 10 is deployed at a target site of the blood vessel. More particularly, the balloon catheter 10 is employed to deliver an anti-proliferative hydrophobic therapeutic agent (such as paclitaxel or rapamycin) to vascular tissue through brief, direct pressure contact at high drug concentration during balloon angioplasty. Such techniques may be employed in treating a total occlusion or a narrowing of passages. Such techniques may also be employed to inhibit hyperplasia and restenosis, as the hydrophobic therapeutic agent may be retained in the target tissue at the delivery site.

The balloon catheter 10 may also be employed in combination with other methods for treating the vasculature, such as with photodynamic therapy or atherectomy. With regard to photodynamic therapy, photodynamic therapy is a procedure where light or irradiated energy is used to kill target cells in a patient. A light-activated photosensitizing hydrophobic therapeutic agent may be delivered to specific areas of tissue by the balloon catheter 10. A targeted light or radiation source selectively activates the hydrophobic therapeutic agent to produce a cytotoxic response and mediate a therapeutic anti-proliferative effect.

With regard to atherectomy, atherectomy is a procedure employed to remove plaque from arteries. More specifically, atherectomy removes plaque from peripheral and coronary arteries. The medical device used for peripheral or coronary atherectomy may be a laser catheter, a rotational atherectomy device such as a Rotablator® (Boston Scientific, Quincy, Mass.), or a direct atherectomy device on the end of a catheter. During atherectomy, a catheter is inserted into the body and advanced through an artery to the area of narrowing. After the atherectomy has removed some of the plaque, balloon angioplasty using the coated balloon catheter 10 may be performed. In addition, stenting may also be performed thereafter, or simultaneous with expansion of the coated expandable balloon 12 as described above.

EXAMPLES

The following examples include embodiments of balloon catheters and coating layers within the scope of the present disclosure. While the following examples are considered to embody the present disclosure, the examples should not be interpreted as limitations upon the present disclosure.

Example 1

Preparation of Coating Solutions

Experimental Protocol. Coating solutions for balloon catheters were prepared. More particularly, coating solutions for balloon catheters including Formulations I-XI were prepared. Formulations I-XI are set forth in Table 1 below.

TABLE 1

| FORMULATION NO. | HYDROPHOBIC THERAPEUTIC AGENT | ADDITIVE(S) | SOLVENT |
| --- | --- | --- | --- |
| I | Paclitaxel | Gluconolactone | Acetone, Ethanol, Water |
| II | Paclitaxel | Tween 20, N-octanoyl N-methylglucamine | Acetone, Ethanol |
| III | Paclitaxel | Tween 20, Sorbitol | Acetone, Ethanol, Water |
| IV | Paclitaxel | Meglumine, Gensitic Acid | Acetone, Ethanol |
| V | Paclitaxel | Lactobionic Acid, Diethanolamine | Acetone, Ethanol, Water |
| VI | Paclitaxel | N-Octanoyl-N-methylglucamine | Acetone, Ethanol |
| VII | Paclitaxel | Meglumine, Lactic Acid | Acetone, Ethanol, Water |
| VIII | Paclitaxel | Gensitic Acid, Diethanolamine | Acetone, Ethanol, Water |
| IX | Paclitaxel | Triton X-100, N-heptanoyl N-Methylglucamine | Acetone, Ethanol |
| X | Paclitaxel | Ultravist 370 | Ethanol, Acetone |
| XI | Paclitaxel | N/A | Ethanol, Acetone |

Preparation of Coating Solution Formulations I-XI in Table 1 is set forth below.

Formulation I. 50-100 mg (0.06-0.12 mmole) paclitaxel, 1-1.6 ml acetone, 1-1.6 ml ethanol, 0.4-1.0 ml water, and 50-200 mg gluconolactone were mixed.

Formulation II. 35-70 mg (0.042-0.084 mmole) paclitaxel, 0.5-1.0 ml acetone, 0.5-1.0 ml ethanol, 35-70 mg Tween 20, and 35-70 mg N-octanoyl N-methylglucamine were mixed.

Formulation III. 35-70 mg (0.042-0.084 mmole) paclitaxel, 0.4-1.0 ml acetone, 0.4-1.0 ml ethanol, 0.2-0.4 ml water, 35-70 mg Tween 20, and 35-70 mg sorbitol were mixed.

Formulation IV. 40-80 mg (0.048-0.096 mmole) paclitaxel, 0.5-1.0 ml acetone, 0.5-1.0 ml ethanol, 40-80 mg meglumine, and 32-64 mg gensitic acid (equal molar ratio with meglumine) were mixed.

Formulation V. 35-70 mg (0.042-0.084 mmole) paclitaxel, 0.4-0.8 ml acetone, 0.4-0.8 ml ethanol, 0.25-0.50 ml water, 35-70 mg lactobionic acid, and 10-20 mg diethanolamine (equal molar ratio with lactobionic acid) were mixed.

Formulation VI. 35-70 mg (0.042-0.084 mmole) paclitaxel, 0.5-1.0 ml acetone, 0.5-1.0 ml ethanol, and 70-140 mg N-octanoyl N-methylglucamine were mixed.

Formulation VII. 35-70 mg (0.042-0.084 mmole) paclitaxel, 0.4-0.8 ml acetone, 0.4-0.8 ml ethanol, 0.2-0.4 ml water, 35-70 mg meglumine, and 18-36 mg lactic acid (equal molar ratio with meglumine) were mixed.

Formulation VIII. 50-100 mg (0.06-0.12 mmole) paclitaxel, 0.8-1.6 ml acetone, 0.8-1.6 ml ethanol, 0.4-1.0 ml water, 50-100 mg gensitic acid, and 30-60 mg diethanolamine (equal molar ratio with gensitic acid) were mixed.

Formulation IX. 35-70 mg (0.042-0.084 mmole) paclitaxel, 0.5-1.0 ml acetone, 0.5-1.0 ml ethanol, 35-70 mg Triton X-100, and 35-70 mg N-heptanoyl N-methylglucamine were mixed.

Formulation X—Comparison Solution 1. 50 mg (0.06 mmole) paclitaxel, 1 ml ethanol, 0.2 ml acetone, 0.042 ml Ultravist 370 were mixed.

Formulation XI—Comparison Solution 2. 40 mg (0.048 mmole) paclitaxel, 0.5 ml ethanol, 0.5 ml acetone were mixed.

Example 2

Coating of PTCA Balloon Catheters

Experimental Protocol. PTCA balloon catheters were coated with the coating solutions including Formulations I-XI prepared in Example 1. More specifically, 6 PTCA balloon catheters (3.5 and 3.0 mm in diameter and 20 mm in length) were inflated at 1-3 atm. The inflated balloon was loaded with one of the coating solutions including Formulations I-XI from Example 1. A sufficient amount of paclitaxel on the balloon (3 microgram per square mm) was obtained. The inflated balloons were folded, and then dried. The coated folded balloon was then rewrapped and sterilized for animal testing.

Example 3

Delivering Paclitaxel from the Coated PTCA Balloon Catheters to Target Sites

Experimental Protocol. Paclitaxel was delivered to target sites in the coronary vasculature of pigs from the coated PTCA balloon catheters prepared in Example 2. More specifically, the coated PTCA balloon catheters from Example 2 were inserted into a target site in the coronary vasculature (LAD, LCX and RCA) of a 25-45 pound pig. The balloons were inflated to about 12 atm. The overstretch ratio (the ratio of balloon diameter to vessel diameter) was about 1.15-1.20. The paclitaxel delivered into the target tissue during 30-60 seconds of inflation. The balloon catheter was then deflated and withdrawn from the animal body. The target blood vessel was harvested 0.25-24 hours after the procedure. The paclitaxel content in the target tissue and the residual paclitaxel remaining on the balloon were analyzed by tissue extraction and HPLC.

In some of these animal studies, a stent was crimped on the coated balloon catheters from Example 2 prior to deployment. In chronic animal tests, angiography was performed before and after all interventions and at 28-35 days after the procedure. Luminal diameters were measured and late lumen loss was calculated. Late lumen loss is the difference between the minimal lumen diameter measured after a period of follow-up time (usually weeks to months after an intervention, such as angioplasty and stent placement in the case of this example) and the minimal lumen diameter measured immediately after the intervention. Restenosis may be quantified by the diameter stenosis, which is the difference between the mean lumen diameters at follow-up and immediately after the procedure divided by the mean lumen diameter immediately after the procedure. The animal test results for the Formulations I-XI from Example 1 are reported below.

Experimental Results. All data is an average of five or six experimental data points.

Formulation I. The paclitaxel content of the Formulation I from Example 1 on the 3.5 mm balloon catheters was 3.26 µg/mm$^2$. After the procedure, the paclitaxel on the balloon was 15.92 µg, or 2.3% of the total paclitaxel loaded on the balloon. The paclitaxel content in tissue harvested 15-30 minutes after the procedure was 64.79 µg, or 9.2% of the total paclitaxel content originally loaded on the balloon. When an 18 mm stent was deployed by the coated balloon, the residual paclitaxel on the balloon was 31.96 µg, or 4.5% of paclitaxel load, and the paclitaxel content in tissue harvested 15-30 minutes after the procedure was 96.49 µg, or 13.7% of paclitaxel load. The stretch ratio is 1.3 in the procedure. The late lumen loss after 28-35 days was 0.10 (sd 0.2) mm. The diameter stenosis is 3.3%.

Formulation II. The paclitaxel content of the Formulation II from Example 1 on the 3.5 mm balloon catheters was 3.08 µg/mm$^2$. After the procedure, the residual paclitaxel on the balloon was 80.58 µg, or 11.4% of the total paclitaxel load. The paclitaxel content in tissue harvested 15-30 minutes after the procedure was 42.23 µg, or 6.0% of the total paclitaxel load. After 28-35 days late lumen loss was 0.30 (sd 0.23) mm. The diameter stenosis was 5.4%.

Formulation III. The paclitaxel content of the Formulation III from Example 1 on the 3.5 mm balloon catheters was 3.61 µg/mm$^2$. After the procedure, the residual paclitaxel on the balloon was 174.24 µg, or 24.7% of the total paclitaxel load. The paclitaxel content in tissue harvested 15-30 minutes after the procedure was 83.83 µg, or 11.9% of the total drug load. When deployed with a pre-crimped 18 mm stent, the residual paclitaxel on the balloon is 114.53 µg, or 16.1% of the total paclitaxel load, and the paclitaxel content in tissue harvested 15-30 minutes post procedure was 147.95 µg, or 18.1% of the total paclitaxel load. The stretch ratio was 1.3 in the procedure. The late lumen loss after 28-35 days was 0.10 (sd 0.1) mm. The diameter stenosis was 3.4%.

Formulation IV. The paclitaxel content of the Formulation IV from Example 1 on the 3.5 mm balloon catheters was 4.71 µg/mm$^2$. After the procedure, the residual paclitaxel on the balloon was 44.39 µg, or 6.3% of the total paclitaxel load. The paclitaxel content in the tissue harvested 15-30 minutes after the procedure was 77.87 µg, or 11.0% of the total paclitaxel load. After 28-35 days late lumen loss was 0.23 (sd 0.44) mm. The diameter stenosis was 7.3%.

Formulation V. The paclitaxel content of the Formulation V from Example 1 on the 3.5 mm balloon catheters was 3.85

μg/mm². After the procedure, residual paclitaxel on the balloon was 24.59 μg, or 3.5% of the total paclitaxel load. The paclitaxel content in tissue harvested 15-30 minutes after the procedure was 37.97 μg, or 5.4% of the total paclitaxel load. After 28-35 days late lumen loss was 0.33 (sd 0.14) mm. The diameter stenosis was 6.7%.

Formulation VI. The paclitaxel content of the Formulation VI from Example 1 on the 3.5 mm balloon catheters was 3.75 μg/mm². After the procedure, residual paclitaxel on the balloon was 0.82 μg, or 0.1% of the total paclitaxel load. The paclitaxel content in tissue harvested 60 minutes after the procedure was 45.23 μg, or 5.5% of the total paclitaxel load. After 28-35 days late lumen loss was 0.49 (sd 0.26) mm. The diameter stenosis was 11.3%.

Formulation VII. The paclitaxel content of the Formulation VII from Example 1 on the 3.5 mm balloon catheters was 3.35 μg/mm². After the procedure, the residual paclitaxel on the balloon was 62.07 μg, or 7.5% of the total paclitaxel load. The paclitaxel content in tissue harvested 60 minutes after the procedure was 40.55 μg, or 4.9% of the total paclitaxel load. After 28-35 days late lumen loss was 0.47 (sd 0.33) mm. The diameter stenosis was 9.9%.

Formulation VIII. The paclitaxel content of the Formulation VIII from Example 1 on the 3.5 mm balloon catheters was 3.41 μg/mm². After the procedure, residual paclitaxel on the balloon was 50.0 μg, or 6.0% of the total paclitaxel load. The paclitaxel content in tissue harvested 60 minutes post procedure was 26.72 μg, or 3.2% of the total paclitaxel load. After 28-35 days late lumen loss was 0.36 (sd 0.41) mm. The diameter stenosis was 9.3%.

Formulation IX. The paclitaxel content of the Formulation IX from Example 1 on the 3.5 mm balloon catheters was 3.10 μg/mm². After the procedure, residual paclitaxel on the balloon was 1.9% of the total paclitaxel load. The paclitaxel content in tissue harvested 2 hours after the procedure was 34.17 μg, or 5.0% of the total paclitaxel load. In tissue harvested 24 hours after the procedure, the paclitaxel content in tissue was 28.92 μg, or 4.2% of the total paclitaxel load.

Control Formulation. The drug content of control formulation (uncoated balloon) on the 3.5 mm balloon catheters was 0.0 μg/mm². After the procedure, residual drug on the balloon was 0% of the total drug load. The drug content in tissue harvested 15 minutes after the procedure was 0 μg. In tissue harvested 24 hours after the procedure, the drug content in tissue was 0 μg. After 28-35 days late lumen loss was 0.67 (sd 0.27) mm. The diameter stenosis is 20.8%. In the second repeat experiment, the stretch ratio was 1.3. The late lumen loss was 1.1 (sd 0.1). The diameter stenosis was 37.5%.

Formulation X—Comparison Solution 1. The paclitaxel content of the Formulation X from Example 1 on the 3.5 mm balloon catheters was 3.21 μg/mm². After the procedure, residual paclitaxel on the balloon was 13.52 μg, or 1.9% of the total paclitaxel load. The paclitaxel content in the tissue was 28.32 μg, or 4.0% of the total paclitaxel load. When the balloon was deployed with a pre-crimped 18 mm stent, residual paclitaxel on the balloon was 26.45 μg, or 3.7% of the total paclitaxel load. The paclitaxel content in tissue was 113.79 μg, or 16.1% of drug load. After 28-35 days, late lumen loss was 0.27 (sd 0.15) mm. The diameter stenosis was 7.1%.

Formulation XI—Comparison Solution 2. The paclitaxel content of the Formulation XI (without additive) on the 3.5 mm balloon catheters was 4.22 μg/mm². After the procedure, residual paclitaxel on the balloon was 321.97 μg, or 45.6% of the total paclitaxel load. The paclitaxel content in the tissue was 12.83 μg, or 1.8% of the total paclitaxel load.

Surprisingly, the concentration of paclitaxel absorbed by porcine coronary artery tissue after deployment of balloons coated with the Formulations I-IX from Example 1 according to embodiments of the present disclosure was higher than that delivered by balloons coated with the Formulation X from Example 1 and higher than those coated with paclitaxel alone, the Formulation XI from Example 1. The late lumen loss after 28-35 days follow up was less than the control (uncoated balloon).

What is claimed is:

1. A balloon catheter for delivering a therapeutic agent to a blood vessel while the balloon catheter is deployed at a target site of the blood vessel, the balloon catheter comprising:
   an elongate member having a guide-wire lumen, an inflation lumen, a proximal end, and a distal end,
   an expandable balloon attached to the distal end of the elongate member and in fluidic communication with the inflation lumen;
   a hub attached to the proximal end, the hub having an inflation port connected to the inflation lumen and a guide-wire port connected to the guide-wire lumen; and
   a coating layer overlying an exterior surface of the expandable balloon, wherein:
   the coating layer comprises a total drug load of a hydrophobic therapeutic agent and a combination of additives comprising a first additive and a second additive;
   the hydrophobic therapeutic agent is one of paclitaxel, rapamycin, or combinations thereof;
   the first additive is one of PEG sorbitan monolaurates, PEG sorbitan monooleates, PEG sorbitan monopalmitates, PEG sorbitan monostearates, or combinations thereof; and
   the second additive is one of sorbitol, sorbitan, xylitol, gluconolactone, lactobionic acid, or combinations thereof.

2. The balloon catheter of claim 1, wherein the hydrophobic therapeutic agent is paclitaxel.

3. The balloon catheter of claim 1, wherein the hydrophobic therapeutic agent is rapamycin.

4. The balloon catheter of claim 1, wherein the hydrophobic therapeutic agent is uniformly distributed in the coating layer.

5. The balloon catheter of claim 1, wherein the total drug load of the hydrophobic therapeutic agent is from 1 μg to 20 μg per square millimeter of the expandable balloon.

6. The balloon catheter of claim 1, wherein the total drug load of the hydrophobic therapeutic agent is from 2.5 μg to 6 μg per square millimeter of the expandable balloon.

7. The balloon catheter of claim 1, wherein the first additive is a PEG sorbitan monolaurate.

8. The balloon catheter of claim 7, wherein the PEG sorbitan monolaurate is PEG-20 sorbitan monolaurate.

9. The balloon catheter of claim 1, wherein the first additive is a PEG sorbitan monooleate.

10. The balloon catheter of claim 9, wherein the PEG sorbitan monooleate is PEG-20 sorbitan monooleate.

11. The balloon catheter of claim 1, wherein the first additive is one of PEG-20 sorbitan monolaurate, PEG-20 sorbitan monooleate, or combinations thereof.

12. The balloon catheter of claim 1, wherein the second additive is one of sorbitol, gluconolactone, or combinations thereof.

13. The balloon catheter of claim 1, wherein the second additive is sorbitol.

14. The balloon catheter of claim 1, wherein the second additive is gluconolactone.

15. The balloon catheter of claim 1, wherein the ratio by weight of the combination of additives in the coating layer to the hydrophobic therapeutic agent in the coating layer is about 10 to 0.5.

16. The balloon catheter of claim 1, wherein:
the coating layer consists essentially of the hydrophobic therapeutic agent, the first additive, and the second additive;
the hydrophobic therapeutic agent is paclitaxel;
the first additive is one of PEG-20 sorbitan monolaurate, PEG-20 sorbitan monooleate, or combinations thereof; and
the second additive is one of sorbitol, gluconolactone, or combinations thereof.

17. The balloon catheter of claim 1, wherein:
the coating layer consists essentially of the hydrophobic therapeutic agent, the first additive, and the second additive;
the hydrophobic therapeutic agent is paclitaxel;
the first additive is PEG-20 sorbitan monolaurate; and
the second additive is sorbitol.

18. The balloon catheter of claim 1, wherein:
the coating layer consists essentially of the hydrophobic therapeutic agent, the first additive, and the second additive;
the hydrophobic therapeutic agent is paclitaxel;
the second additive is gluconolactone; and
the total drug load of the hydrophobic therapeutic agent is from 2 µg to 6 µg per square millimeter of the expandable balloon.

19. The balloon catheter of claim 1, wherein the coating layer has a thickness of from about 0.1 µm to 15 µm.

20. A balloon catheter for delivering a therapeutic agent to a blood vessel while the balloon catheter is deployed at a target site of the blood vessel, the balloon catheter comprising:
an elongate member having a guide-wire lumen, an inflation lumen, a proximal end, and a distal end,
an expandable balloon attached to the distal end of the elongate member and in fluidic communication with the inflation lumen;
a hub attached to the balloon catheter at the proximal end, the hub having an inflation port connected to the inflation lumen and a guide-wire port connected to the guide-wire lumen; and
a coating layer overlying an exterior surface of the expandable balloon, wherein:
the coating layer comprises a total drug load of a hydrophobic therapeutic agent and a combination of additives comprising a first additive and a second additive;
the total drug load of the hydrophobic therapeutic agent is from 2.5 µg to 6 µg per square millimeter of the expandable balloon;
the hydrophobic therapeutic agent is one of paclitaxel, rapamycin, or combinations thereof;
the first additive is one of PEG-20 sorbitan monolaurate, PEG-20 sorbitan monooleate, PEG-20 sorbitan monopalmitate, PEG-20 sorbitan mono stearate, or combinations thereof;
the second additive is one of sorbitol, gluconolactone, or combinations thereof; and
the ratio by weight of the combination of additives in the coating layer to the hydrophobic therapeutic agent in the coating layer is about 10 to 0.5.

* * * * *